United States Patent [19]
Ito

[11] Patent Number: 6,052,487
[45] Date of Patent: Apr. 18, 2000

[54] METHOD AND APPARATUS FOR COMPRESSING IMAGE SIGNALS

[75] Inventor: Wataru Ito, Kanagawa-ken, Japan

[73] Assignee: Fuji Photo Film Co., Ltd., Kanagawa-ken, Japan

[21] Appl. No.: 08/136,254

[22] Filed: Oct. 15, 1993

[30] Foreign Application Priority Data

Oct. 15, 1992 [JP] Japan ................................... 4-277542
Oct. 15, 1992 [JP] Japan ................................... 4-277543

[51] Int. Cl.$^7$ .............................. G06K 9/00; G06K 9/36
[52] U.S. Cl. ........................ 382/239; 382/232; 382/128; 358/430
[58] Field of Search ................................ 382/56, 6, 232, 382/239, 128; 364/413.26, 413.23; 250/327.2, 581, 582, 584, 587, 591; 358/428, 430; 348/384

[56] References Cited

U.S. PATENT DOCUMENTS

| | | | |
|---|---|---|---|
| 4,258,264 | 3/1981 | Kotera et al. ........................... | 250/484 |
| 4,568,973 | 2/1986 | Ishida ...................................... | 358/111 |
| 4,941,194 | 7/1990 | Shimura .................................... | 382/56 |
| 5,006,708 | 4/1991 | Itoh et al. ................................. | 382/31 |
| 5,028,784 | 7/1991 | Arakawa et al. .................... | 250/327.2 |
| 5,086,489 | 2/1992 | Shimura .................................... | 382/56 |

FOREIGN PATENT DOCUMENTS 56-11395 2/1981 Japan .............................. G21K 4/00

*Primary Examiner*—Matthew Bella
*Attorney, Agent, or Firm*—Sughrue, Mion, Zinn Macpeak & Seas, PLLC

[57] ABSTRACT

When an image signal representing a radiation image is compressed and decompressed, and a visible radiation image is reproduced from the decompressed image signal, a compressing process to be employed is changed in accordance with conditions, under which the image signal before being subjected to compression processing has been generated. A moire is thereby prevented from occurring on a reproduced radiation image, the compression processing speed and the compressibility are kept high, and the image quality (the sharpness) of the reproduced radiation image is prevented from becoming worse.

26 Claims, 19 Drawing Sheets

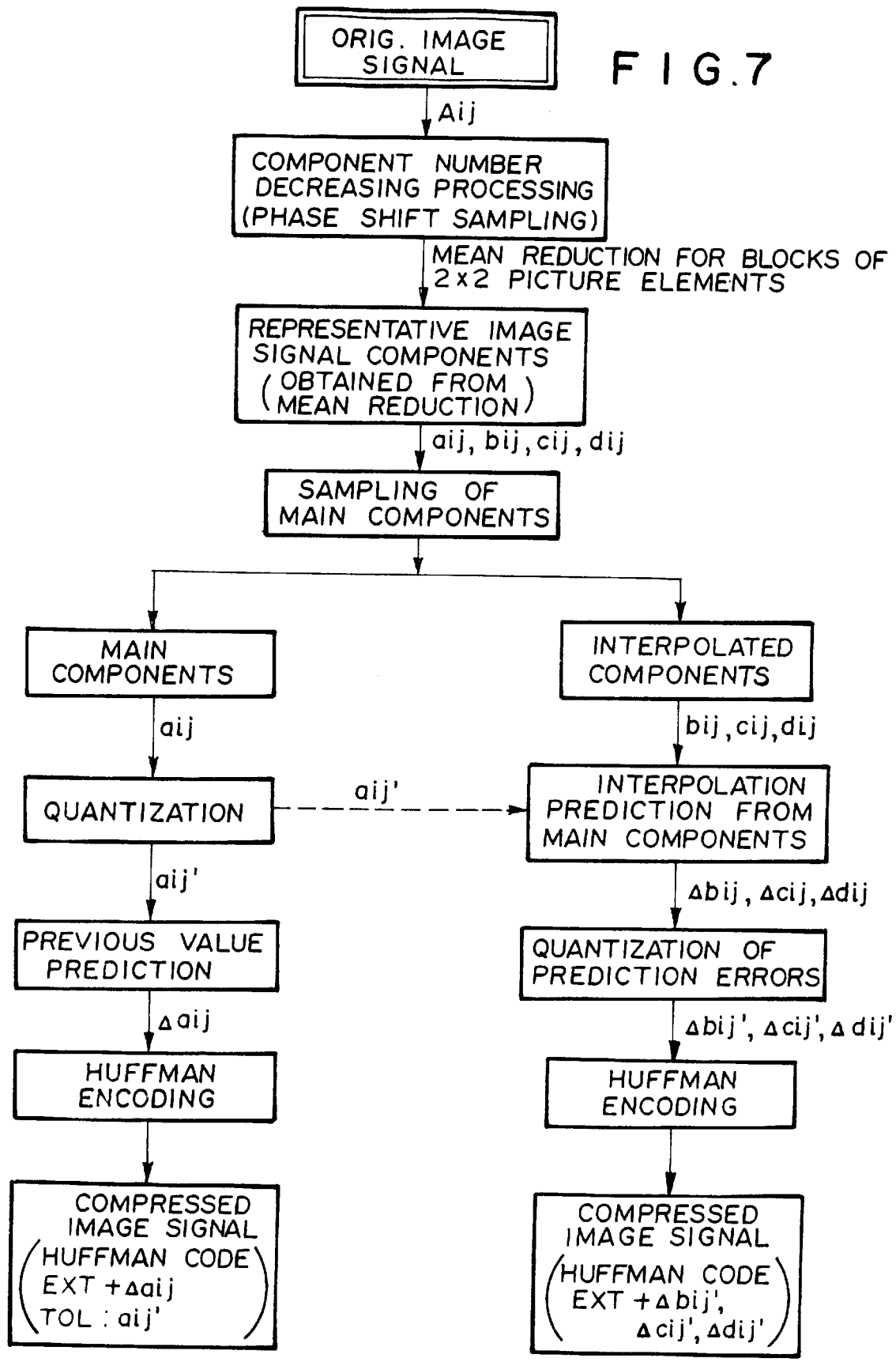

FIG. 11

| $a_{11}$ | | $\Delta a_{12}$ | | $\Delta a_{13}$ |
|---|---|---|---|---|
| | | | | |
| $a_{21}$ | | $\Delta a_{22}$ | | $\Delta a_{23}$ |
| | | | | |
| $a_{31}$ | | $\Delta a_{32}$ | | $\Delta a_{33}$ |

FIG. 12

| ⓐ$_{11}$ | $\Delta b_{11}$ | ⓐ$_{12}$ | $\Delta b_{12}$ | ⓐ$_{13}$ |
|---|---|---|---|---|
| $\Delta c_{11}$ | $\Delta d_{11}$ | $\Delta c_{12}$ | $\Delta d_{12}$ | |
| ⓐ$_{21}$ | $\Delta b_{21}$ | ⓐ$_{22}$ | $\Delta b_{22}$ | ⓐ$_{23}$ |
| $\Delta c_{21}$ | $\Delta d_{21}$ | $\Delta c_{22}$ | $\Delta d_{22}$ | |
| ⓐ$_{31}$ | $\Delta b_{31}$ | ⓐ$_{32}$ | $\Delta b_{32}$ | ⓐ$_{33}$ |

FIG. 16

| $a_{11}$ | Ⓐ$_{12}$ | $b_{11}$ | | $a_{12}$ | | $b_{12}$ |
|---|---|---|---|---|---|---|
| | Ⓐ$_{22}$ | Ⓐ$_{23}$ | | | | |
| | $c_{11}$ | Ⓐ$_{33}$ | $d_{11}$ | | $c_{12}$ | |
| | | | | | | |
| $a_{12}$ | | $b_{12}$ | | $a_{22}$ | | $b_{22}$ |

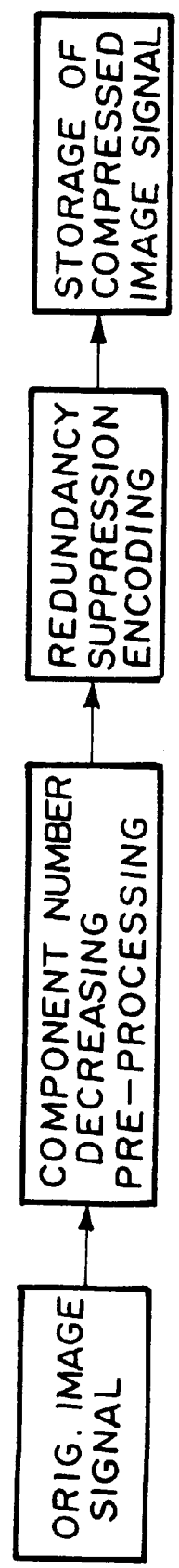
F I G. 17A
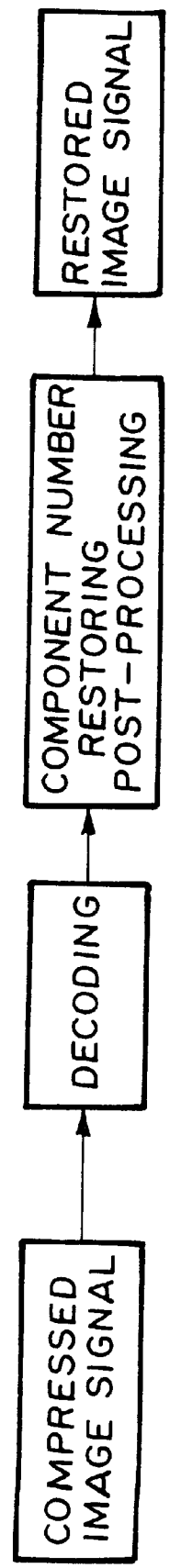
F I G. 17B

FIG. 19

|     | $X_{11}$ | $X_{12}$ | $X_{13}$ | $X_{14}$ | $X_{15}$ | $X_{16}$ |
|-----|----------|----------|----------|----------|----------|----------|
| $L_1$ | $a_{11}$ | $a_{12}$ | $a_{13}$ | $a_{14}$ | $a_{15}$ | $a_6$ |
| $L_2$ | $a_{21}$ | $a_{22}$ | $a_{23}$ | $a_{24}$ | $a_{25}$ | $a_{26}$ |
| $L_3$ | $a_{31}$ | $a_{32}$ | $a_{33}$ | $a_{34}$ | $a_{35}$ | $a_{36}$ |

| $a_{11}$ | $\Delta a_{12} = a_{12} - a_{11}$ | $\Delta a_{13} = a_{13} - a_{12}$ | $\Delta a_{14} = a_{14} - a_{13}$ |
|----------|-----------------------------------|-----------------------------------|-----------------------------------|
| $a_{21}$ | $\Delta a_{22} = a_{22} - a_{21}$ | $\Delta a_{23} = a_{23} - a_{22}$ | $\Delta a_{24} = a_{24} - a_{23}$ |
| $a_{31}$ | $\Delta a_{32} = a_{32} - a_{31}$ | $\Delta a_{33} = a_{33} - a_{32}$ | $\Delta a_{34} = a_{34} - a_{33}$ |

FIG. 21

| TOI | $a_{11}'$ | $\Delta a_{12}'$ | $\Delta a_{13}'$ | -------- | $\Delta a_{1n}'$ | TOL | $a_{21}'$ |

| $\Delta a_{2n}'$ | TOL | $a_{31}'$ | $\Delta a_{32}'$ | -------- |

METHOD AND APPARATUS FOR COMPRESSING IMAGE SIGNALS

BACKGROUND OF THE INVENTION

1. Field of the Invention

This invention relates to a method and apparatus for compressing an image signal representing a radiation image. This invention also relates to a method and apparatus for reproducing a radiation image from an image signal representing a radiation image, and more particularly to a method and apparatus for reproducing a radiation image from an image signal, which has been subjected to interpolation processing carried out for enlarging or reducing the radiation image.

2. Description of the Prior Art

Radiation images recorded on sheets of X-ray film have heretofore been read out by use of film digitizers, or the like, and electric image signals representing the radiation images are thereby obtained. Visible radiation images are then reproduced from the image signals and displayed on display devices, such as cathode ray tube (CRT) display devices.

Also, when certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays, such as visible light, light is emitted by the phosphor in proportion to the amount of energy stored thereon during its exposure to the radiation. A phosphor exhibiting such properties is referred to as a stimulable phosphor.

As disclosed in U.S. Pat. No. 4,258,264 and Japanese Unexamined Patent Publication No. 56(1981)-11395, it has been proposed to use stimulable phosphors in radiation image recording and reproducing systems. Specifically, a radiation image of an object, such as the human body, is stored on a sheet provided with a layer of the stimulable phosphor (hereinafter referred to as a stimulable phosphor sheet). The stimulable phosphor sheet is then scanned with stimulating rays, such as a laser beam, which cause it to emit light in proportion to the amount of energy stored thereon during its exposure to the radiation. The light emitted by the stimulable phosphor sheet when it is exposed to the stimulating rays is photoelectrically detected and converted into an electric image signal. The image signal is then used during the reproduction of the radiation image of the object as a visible image on a recording material, such as photographic film, on a display device, such as a cathode ray tube (CRT) display device, or the like.

When a radiation image of an object is recorded on a recording medium, such as X-ray film or a stimulable phosphor sheet, a grid is often located between the object and the recording medium such that radiation scattered by the object may not impinge upon the recording medium. The grid is constituted of bars of a radiation-impermeable material, such as lead, and bars of a radiation-permeable material, such as aluminum, which are alternately located in parallel at small pitches of approximately 4.0 bars/mm. When the grid is used during the recording of a radiation image of an object on a recording medium, radiation scattered by the object is prevented from impinging upon the recording medium, and therefore the contrast of the radiation image of the object can be kept high. However, a grid image having a striped pattern is recorded together with the object image on the recording medium.

In general, in radiation image read-out apparatuses, wherein an image signal is detected from a recording medium which has a radiation image recorded thereon, light which is emitted from the recording medium and which carries information about the radiation image is photoelectrically detected and converted into an image signal. The image signal is then sampled at sampling intervals of $\Delta x=1/(2 \cdot fss)$ corresponding to the spatial frequency, which is the maximum of a spatial frequency range necessary for image information. The spatial frequency, which is the maximum of a spatial frequency range necessary for image information, is herein denoted by fss. The sampled image signal is then digitized. In cases where the radiation image comprises the object image and a grid image superposed upon the object image, the image signal obtained in the manner described above includes not only the information representing the radiation image of the object but also noise which is caused to occur by the grid image.

FIG. 6A is a graph showing the spatial frequency characteristics of a radiation image, which has been recorded on a recording medium and which comprises an object image and a grid image superposed upon the object image, in a direction along which the stripes of the striped pattern of the grid image stand side by side. By way of example, it is herein assumed that, during the recording of the radiation image, a grid having the bars of a radiation-impermeable material and the bars of a radiation-permeable material, which are alternately located in parallel at pitches of 4.0 bars/mm, was used. The spatial frequency of the grid image is 4 cycles/mm. Also, it is assumed herein that the spatial frequency fss, which is the maximum of a spatial frequency range necessary for the reproduction of a visible radiation image of the object, is 2.5 cycles/mm.

FIG. 6B is an explanatory graph showing how noise occurs when an image signal is sampled at sampling intervals of $\Delta x=1/(2 \cdot fss)=0.2$ (mm) corresponding to the spatial frequency fss=2.5 (cycles/mm), i.e. is sampled five times per mm. When such sampling intervals are applied, it is possible to obtain information in the spatial frequency region which is below the spatial frequency fss=2.5 (cycles/mm), which is the maximum of a spatial frequency range necessary for the reproduction of a visible radiation image of the object. In FIG. 6B, the same curve as that shown in FIG. 6A is indicated by the solid line. As indicated by the broken line, noise occurs at the position corresponding to 1 cycle/mm, with which the position of the peak occurring at 4 cycles/mm coincides when the curve indicated by the solid line is folded back from the part corresponding to fss=2.5 (cycles/mm). Such noise is referred to as "aliasing." Specifically, as indicated by the broken line in FIG. 6B, aliasing noise corresponding to a spatial frequency of 4 cycles/mm of the grid image occurs at the position corresponding to 1 cycle/mm.

FIG. 6C is a graph showing the spatial frequency characteristics of the radiation image represented by an image signal obtained from the sampling in which sampling intervals of $\Delta x=1/(2 \cdot fss)=0.2$ (mm) are applied. As illustrated in FIG. 6C, the image signal includes the noise corresponding to the grid image and occurring at the position of 1 cycle/mm. Therefore, when a visible image is reproduced from the image signal, a striped pattern having a spatial frequency of 1 cycle/mm occurs on the reproduced visible image.

Therefore, a novel method for generating a radiation image signal has been proposed in, for example, U.S. Pat. No. 5,028,784. With the proposed method, an analog image signal, which has been obtained from an image read-out operation carried out on a recording medium, such as X-ray film or a stimulable phosphor sheet, is sampled at sampling intervals smaller than such sampling intervals that a spatial frequency of aliasing caused to occur by a grid image coincides with a spatial frequency, which is the maximum of a desired spatial frequency range. The sampled image signal is digitized, and a digital original image signal is thereby obtained. Thereafter, the original image signal is subjected to filtering processing for reducing or eliminating the frequency components corresponding to the spatial frequency of the grid image. The original image signal, which has been obtained from the filtering processing, is then sampled at such sampling intervals that the spatial frequency, which is the maximum of the desired spatial frequency range, is set as a Nyquist frequency. In this manner, an image signal to be used in reproducing a visible radiation image is generated.

An image signal representing a radiation image is often subjected to compression processing such that as many image signals as possible can be stored (filed) on a storage medium, such as an optical disk, or such that the efficiency, with which the image signal is transmitted to a desired location, can be kept high. The compressed image signal, which has been obtained from compression processing, is then read from the storage medium or is transmitted to a desired location. Thereafter, the compressed image signal is subjected to decompression processing, and the resulting decompressed image signal is used during the reproduction of a visible radiation image.

Various methods for compressing an image signal have heretofore been used. Recently, various novel methods for compressing an image signal have been proposed in order to enhance the compressibility and to prevent the image quality (the sharpness) from becoming worse. For example, U.S. Pat. No. 4,941,194 discloses a method for compressing a radiation image signal by carrying out redundancy suppression encoding processing on an original image signal representing a radiation image, wherein the improvement comprises the steps of: carrying out pre-processing for decreasing the number of image signal components of the original image signal by an appropriate method, and subjecting the image signal, which has been obtained from the pre-processing, to the redundancy suppression encoding processing.

However, the problems have heretofore been encountered in that a moire often occurs on a visible radiation image reproduced from an image signal, which has been obtained from compression processing and decompression processing. The moire occurs particularly on a visible radiation image reproduced from a radiation image having been recorded by using a grid.

Therefore, a method for compressing an image signal, with which the occurrence of a moire can be prevented, has been proposed in, for example, U.S. Pat. No. 5,086,489. The proposed method for compressing an image signal comprises the steps of:

i) subjecting an original image signal, which is made up of a series of image signal components representing an image, to component number decreasing processing wherein:

a) along each of a plurality of block lines which are set in parallel on an image, blocks each of which comprises a single picture element in the image are set at predetermined intervals, or blocks each of which comprises a plurality of picture elements in the image are set continuously or at predetermined intervals, the blocks being set such that the phases of the blocks located along a block line are shifted from the phases of the blocks located along a neighboring block line, b) a representative image signal component is determined for each block from the image signal component representing the single picture element in each block in cases where each block comprises the single picture element, or a representative image signal component is determined for each block from the image signal components representing the picture elements in each block in cases where each block comprises the plurality of the picture elements, and c) only the representative image signal components corresponding to the blocks are sampled as new image signal components, ii) classifying the new image signal components, which have been obtained from the component number decreasing processing, into main components, which have been sampled at appropriate sampling intervals, and interpolated components other than the main components, and iii) subjecting the interpolated components to interpolation prediction encoding processing based on the main components.

The proposed method for compressing an image signal is very effective to prevent the occurrence of a moire but has the problems in that a comparatively long time is required to carry out the compression processing. Also, further improvements should be made in the compressibility and the image quality (the sharpness).

When a visible radiation image is reproduced from an image signal representing a radiation image, the reproduced image is often reduced or enlarged so as to satisfy the requirements of, in particular, diagnoses, restrictions by the image reproducing apparatus, or the like. For example, U.S. Pat. No. 4,568,973 discloses a technique for varying the magnification of reproduction in accordance with the size of a recording medium, such as a stimulable phosphor sheet, which was used during the image recording operation, in cases where the output size in an image reproducing apparatus is fixed.

Ordinarily, in cases where a radiation image represented by a digital image signal is to be enlarged, interpolation processing is carried out on the image signal, and an image signal representing an enlarged image is thereby formed. In cases where a radiation image is to be reduced, basically, the digital image signal may be thinned out. In general, in such cases, interpolation processing is carried out on the image signal, and then an image signal obtained from the interpolation processing is thinned out such that, for example, various scales of reduction may be achieved.

However, when a radiation image reduced or enlarged by carrying out the interpolation processing is reproduced, the problems occur in that a moire or an artifact occurs on the reproduced radiation image or the sharpness of the reproduced radiation image becomes markedly low. The moire occurs particularly on a visible radiation image reproduced from a radiation image having been recorded by using a grid. Also, the artifact occurs particularly when a radiation image is reproduced from an image signal, which has been obtained from irreversible compression processing.

SUMMARY OF THE INVENTION

The primary object of the present invention is to provide a method for compressing an image signal, wherein a moire due to a grid image is prevented from occurring on a reproduced radiation image, compression processing is carried out quickly, the compressibility is kept high, and the image quality (the sharpness) of the reproduced radiation image is prevented from becoming worse.

Another object of the present invention is to provide an apparatus for carrying out the method for compressing an image signal.

A further object of the present invention is to provide a method for reproducing a radiation image, wherein a moire or an artifact is prevented from occurring on a radiation image reproduced from an image signal, which has been obtained from interpolation processing, and the sharpness of the reproduced image is prevented from becoming low.

A further object of the present invention is to provide an apparatus for carrying out the method for reproducing a radiation image.

The present invention provides a method for compressing an image signal representing a radiation image, comprising changing a compressing process, which is to be employed during compression processing carried out on an image signal, in accordance with conditions, under which the image signal before being subjected to the compression processing has been generated.

The term "conditions, under which an image signal before being subjected to compression processing has been generated" as used herein means, specifically, whether the image signal has or has not been subjected to processing for eliminating a grid image, e.g. the filtering processing and the resampling processing described in U.S. Pat. No. 5,028,784.

The present invention also provides an apparatus for compressing an image signal representing a radiation image, comprising a means capable of carrying out each of a plurality of compressing processes, and a means for changing a compressing process, which is to be employed during compression processing carried out on an image signal, in accordance with conditions, under which the image signal before being subjected to the compression processing has been generated.

In cases where an image signal has been generated without being subjected to processing for eliminating the grid image, if the image signal is directly used in reproducing a visible radiation image, there will be the risk that a moire occurs on the reproduced radiation image. Therefore, as for such an image signal, a compressing process having the effects of restricting the occurrence of a moire, e.g. the compressing process disclosed in U.S. Pat. No. 5,086,489, may be carried out. In this manner, the moire can be reliably prevented from occurring on a visible radiation image, which is reproduced from an image signal obtained from decompression processing.

In cases where an image signal has been generated by being subjected to processing for eliminating the grid image, there is no risk that a moire occurs on a radiation image reproduced from the image signal. Therefore, as for such an image signal, a compressing process, which does not have the effects of restricting the occurrence of a moire but is advantageous with respect to the compression processing speed, the compressibility, and the image quality (the sharpness), e.g. the compressing process disclosed in U.S. Pat. No. 4,941,194, may be carried out. In this manner, the compression processing can be carried out quickly, the compressibility can be kept high, and the image quality can be kept good.

As described above, with the method and apparatus for compressing an image signal in accordance with the present invention, the compression processing speed, the compressibility, and the image quality can be enhanced on the average when many image signals representing radiation images are processed. Also, a moire can be reliably prevented from occurring on a reproduced radiation image.

The present invention further provides a method for reproducing a radiation image, wherein interpolation processing is carried out on an image signal representing a radiation image, and a radiation image is then reproduced from an image signal having been obtained from the interpolation processing, the method for reproducing a radiation image comprising the steps of changing characteristics of the interpolation processing in accordance with conditions, under which the image signal before being subjected to the interpolation processing has been generated.

The term "conditions, under which an image signal before being subjected to interpolation processing has been generated" as used herein means, specifically, whether the image signal has or has not been subjected to the filtering processing and the resampling processing described in, for example, U.S. Pat. No. 5,028,784, and whether the image signal has or has not been subjected to the irreversible compression processing described above.

Also, the term "characteristics of interpolation processing" as used herein means, specifically, the order of and coefficients in the interpolation processing. In the method for reproducing a radiation image in accordance with the present invention, only either one of the order of and the coefficients in the interpolation processing may be changed. Alternatively, both of the order of and the coefficients in the interpolation processing may be changed.

The present invention still further provides an apparatus for reproducing a radiation image, which is provided with a means for carrying out interpolation processing on an image signal representing a radiation image, and a means for reproducing a radiation image from an image signal having been obtained from the interpolation processing, wherein the improvement comprises the provision of a means for changing characteristics of the interpolation processing in accordance with conditions, under which the image signal before being subjected to the interpolation processing has been generated.

How a moire is prevented from occurring on a reproduced radiation image in the method and apparatus for reproducing a radiation image in accordance with the present invention will be described hereinbelow. As described above, in cases where a radiation image has been recorded by using a grid, a grid image having a periodic striped pattern is often recorded on the radiation image. (The radiation image has the spatial frequency characteristics as shown in FIG. 6A. As illustrated in FIG. 6A, specific high spatial frequency components due to the grid are contained to a markedly high extent in the radiation image.) Therefore, if interpolation processing is carried out such that the original radiation image may be enlarged or reduced to a scale other than integral multiples, the moire will occur on the reproduced radiation image.

Therefore, basically, as for an image signal which is likely to have the spatial frequency characteristics as shown in FIG. 6A, i.e. as for an image signal which has been generated without being subjected to the filtering processing and the resampling processing described in, for example, U.S. Pat. No. 5,028,784, interpolation processing may be carried out such that the high frequency region may be removed. In this manner, in cases where the image signal is the one which represents a radiation image having been recorded by using a grid, a moire can be prevented from occurring on a reproduced radiation image. Such interpolation processing includes a process of the first order, a process of a higher order in which coefficients are set such that a high frequency region may be removed, and the like.

When the interpolation processing of the first order is carried out on an image signal, the image signal components corresponding to high spatial frequencies are reduced, and the sharpness of the reproduced image becomes low. On the other hand, with the interpolation processing of a higher order, in general, the sharpness of the reproduced image is not caused to become low. Therefore, in cases where a visible image is to be reproduced from an image signal which has been generated by being subjected to the filtering processing and the resampling processing described above, the interpolation processing of a higher order may be employed.

In this manner, the sharpness of the reproduced radiation image can be prevented from becoming low. Also, in such cases, even if the image signal before being subjected to the interpolation processing is the one which represents a radiation image recorded by using a grid, the image signal will contain no or only few components due to the grid by the effects of the filtering processing and the resampling processing. Therefore, even if the interpolation processing of a higher order is carried out, no grid image will appear on the reproduced radiation image.

An artifact, which occurs when the aforesaid irreversible compression processing is carried out on an image signal, is unevenly distributed in the high spatial frequency region. Therefore, as for the image signal having been generated by being subjected to the irreversible compression processing, for example, the interpolation processing of the first order may be employed. In this manner, an artifact can be prevented from occurring on the reproduced radiation image.

BRIEF DESCRIPTION OF THE DRAWINGS

FIG. 7 is a flow chart showing an image signal compressing process, which is employed in an embodiment of the method for compressing an image signal in accordance with the present invention, FIG. 11 is an explanatory view showing a previous value prediction step carried out on the main components, FIG. 12 is an explanatory view showing the interpolation prediction of interpolated components, FIG. 16 is an explanatory view showing how the number of image signal components is restored in an interpolation enlargement step during the decompression processing shown in FIG. 13, FIG. 17A is a process flow chart showing a different image signal compressing process, which is employed in the embodiment of the method for compressing an image signal in accordance with the present invention, FIG. 17B is a process flow chart showing decompression processing which corresponds to the image signal compressing process shown in FIG. 17A, FIG. 19 is an explanatory view showing an image signal obtained from the component number decreasing pre-processing shown in FIG. 18A, FIG. 20 is an explanatory view showing previous value prediction errors, or the like, with respect to the image signal shown in FIG. 19, FIG. 21 is an explanatory view showing how the codes obtained from Huffman encoding of the previous value prediction errors, or the like, shown in FIG. 20 are stored.

DESCRIPTION OF THE PREFERRED EMBODIMENTS

The present invention will hereinbelow be described in further detail with reference to the accompanying drawings.

First, embodiments of the method for compressing an image signal in accordance with the present invention will be described hereinbelow.

Figure 1:
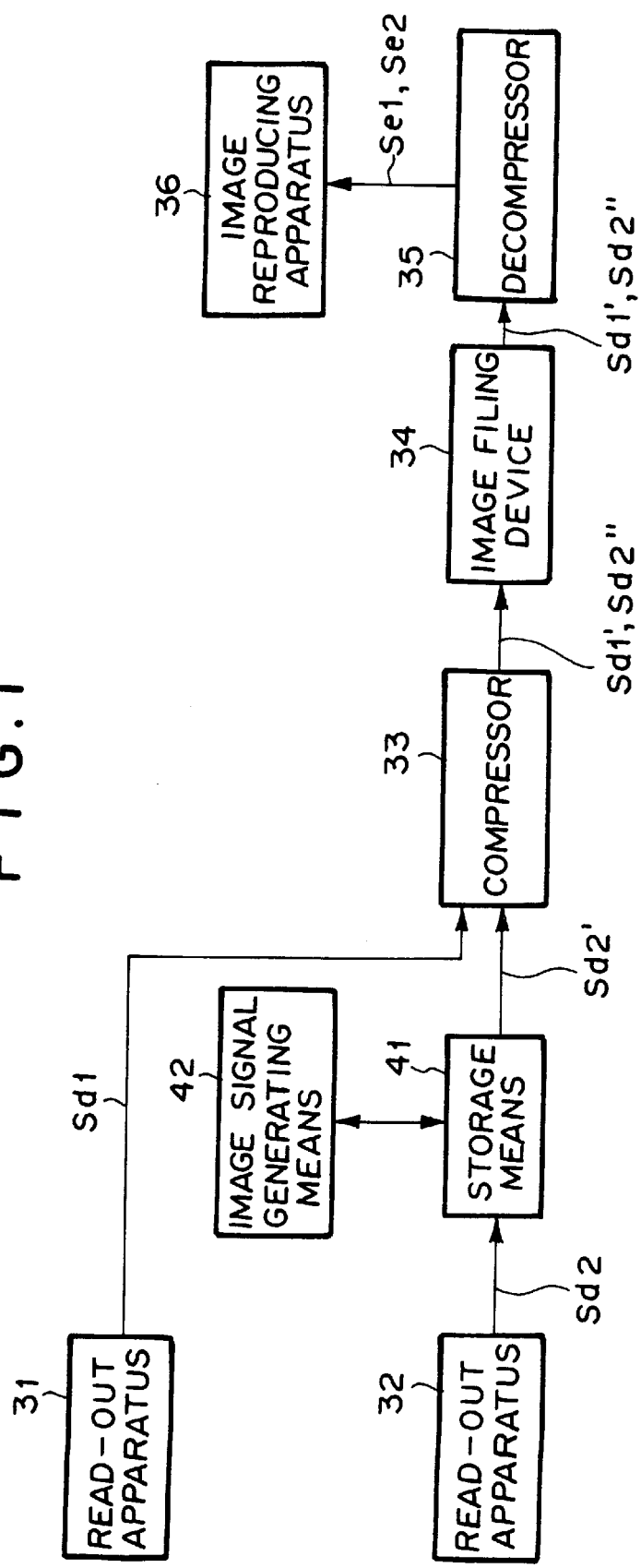
FIG. 1 is a block diagram showing a radiation image read-out and reproducing system for carrying out an embodiment of the method for compressing an image signal in accordance with the present invention.

FIG. 1 shows an example of a radiation image read-out and reproducing system for carrying out an embodiment of the method for compressing an image signal in accordance with the present invention. In the radiation image read-out and reproducing system, a stimulable phosphor sheet is employed as a recording medium. How a radiation image is stored on a stimulable phosphor sheet will be described hereinbelow with reference to FIG. 2.

Figure 2:
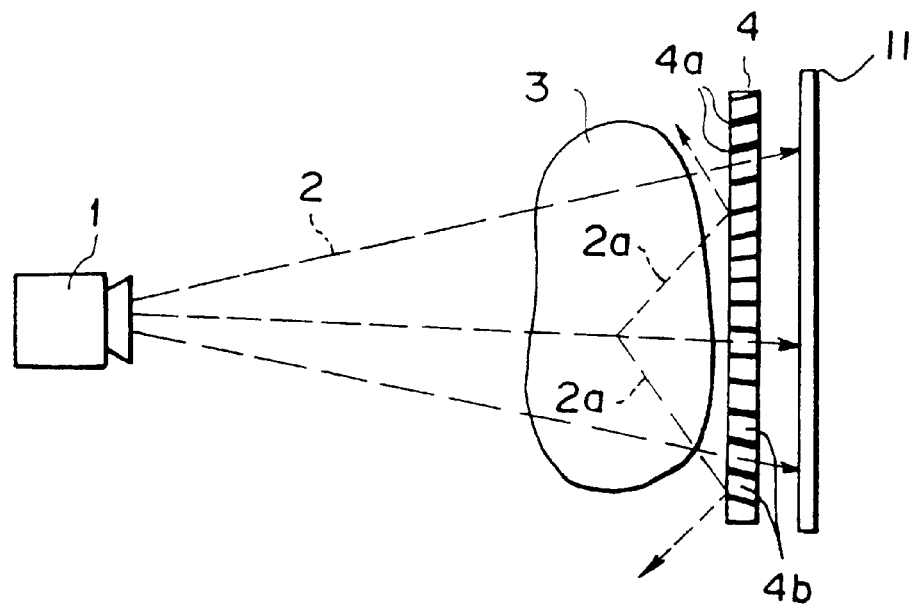
FIG. 2 is a schematic view showing how a radiation image is stored on a stimulable phosphor sheet.

With reference to FIG. 2, radiation 2 is produced by a radiation source 1 and passes through an object 3. Thereafter, the radiation 2 passes through a grid 4 and impinges upon a stimulable phosphor sheet 11. The grid 4 is constituted of lead bars 4a, 4a, . . . and aluminum bars 4b, 4b, . . . which are alternately located in parallel at pitches of 4 bars/mm. The radiation 2 is blocked by the lead bars 4a, 4a, . . . and passes through the aluminum bars 4b, 4b, . . . Therefore, an image of the object 3 and a striped grid image having a pattern of stripes at pitches of 4 stripes/mm are stored on the stimulable phosphor sheet 11. Radiation 2a scattered by the object 3 impinges obliquely upon the grid 4. Therefore, scattered radiation 2a is blocked or reflected by the grid 4 and does not impinge upon the stimulable phosphor sheet 11. Accordingly, a sharp radiation image free of adverse effects of the scattered radiation 2a is stored on the stimulable phosphor sheet 11.

Figure 3:
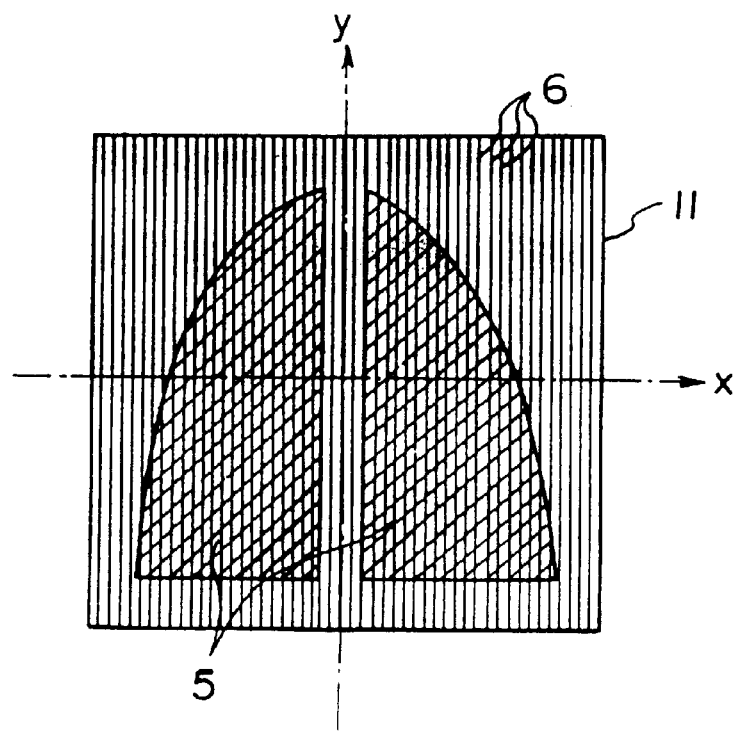
FIG. 3 is a schematic view showing a radiation image which comprises an object image and a striped grid image superposed upon the object image.

FIG. 3 schematically shows a radiation image which has been stored on the stimulable phosphor sheet 11 during the image recording operation using the grid 4. The radiation image comprises an object image 5 (indicated by the oblique lines) and a striped grid image 6 (indicated by vertical stripes) which corresponds to the grid 4 and which is superposed upon the object image 5.

A radiation image recording operation is often carried out without the grid 4 being used. In such cases, the striped grid image 6 is not recorded on the stimulable phosphor sheet 11.

Figure 4:
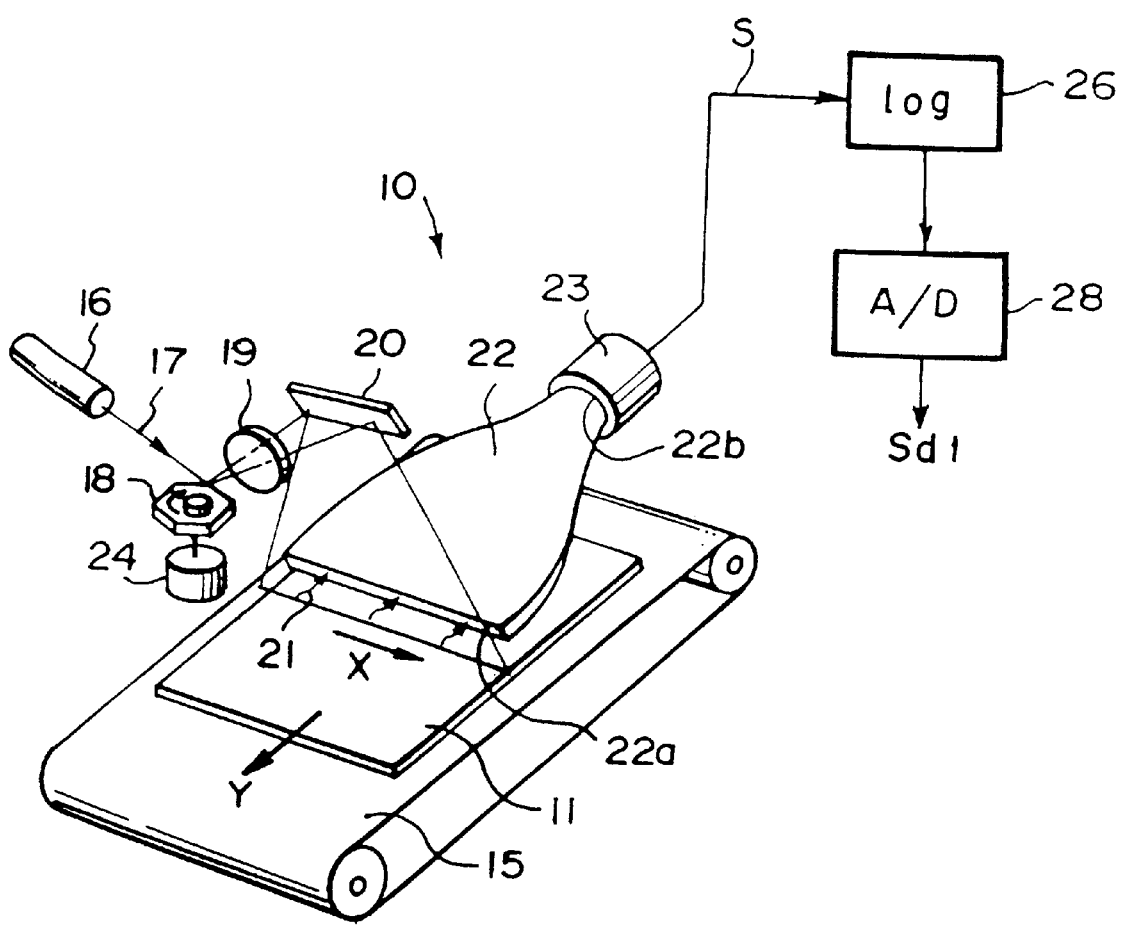
FIG. 4 is a perspective view showing a radiation image read-out apparatus employed in the radiation image read-out and reproducing system of FIG. 1.

The stimulable phosphor sheet 11, on which the radiation image has been stored in the manner described above, is then subjected to an operation for reading out the radiation image in a first radiation image read-out apparatus 31 or a second radiation image read-out apparatus 32 of the radiation image read-out and reproducing system shown in FIG. 1. Both the stimulable phosphor sheet 11, on which the radiation image has been stored by using the grid 4, and the stimulable phosphor sheet 11, on which the radiation image has been stored without the grid 4 being used, are supplied into the radiation image read-out apparatuses 31 and 32. FIG. 4 shows the first radiation image read-out apparatus 31 in detail. How the radiation image is read out from the stimulable phosphor sheet 11 will be described hereinbelow with reference to FIG. 4.

With reference to FIG. 4, the stimulable phosphor sheet 11, on which the radiation image has been stored, is placed at a predetermined position in a read-out means 10. The stimulable phosphor sheet 11 is conveyed in a sub-scanning direction indicated by the arrow Y by a sheet conveyance means 15, which may be constituted of an endless belt, or the like, and which is operated by an operating means (not shown). A laser beam 17 is produced by a laser beam source 16. The laser beam 17 is reflected and deflected by a rotating polygon mirror 18, which is quickly rotated by a motor 24 in the direction indicated by the arrow. Thereafter, the laser beam 17 passes through a converging lens 19, which may be constituted of an fθ lens, or the like. The direction of the optical path of the laser beam 17 is then changed by a mirror 20. The laser beam 17 impinges upon the stimulable phosphor sheet 11 and scans it in a main scanning direction indicated by the arrow X. The main scanning direction is approximately normal to the sub-scanning direction indicated by the arrow Y.

When the stimulable phosphor sheet 11 is exposed to the laser beam 17, the exposed portion of the stimulable phosphor sheet 11 emits light 21 in an amount proportional to the amount of energy stored thereon during its exposure to radiation. The emitted light 21 is guided by a light guide member 22 and photoelectrically detected by a photomultiplier 23. The light guide member 22 is made from a light guiding material, such as an acrylic plate. The light guide member 22 has a linear light input face 22a, which is positioned so that it may extend along the main scanning line on the stimulable phosphor sheet 11, and a ring-shaped light output face 22b, which is positioned so that it may be in close contact with a light receiving face of the photomultiplier 23. The emitted light 21, which has entered the light guide member 22 from its light input face 22a, is guided through repeated total reflection inside of the light guide member 22, emanates from the light output face 22b, and is received by the photomultiplier 23. In this manner, the amount of the emitted light 21 carrying the radiation image is converted into an electric signal by the photomultiplier 23.

An analog output signal S generated by the photomultiplier 23 includes signal components falling within the spatial frequency region above the spatial frequency fss=2.5 (cycles/mm), which is the maximum of a desired spatial frequency range necessary for the reproduction of a visible radiation image having good image quality. Particularly, in cases where the analog output signal S has been detected from the stimulable phosphor sheet 11 on which the radiation image was stored by using the grid 4, the analog output signal S includes the signal components, which represents the grid image 6 shown in FIG. 3 and which fall within the spatial frequency region above the spatial frequency fss. The signal components representing the grid image 6 adversely affect the image quality of a reproduced visible image of the object 3 and should be reduced or eliminated. In this embodiment, the spatial frequency of the grid image is assumed to be 4 cycles/mm.

The analog output signal S is logarithmically amplified by a logarithmic amplifier 26. In an A/D converter 28, the amplified analog output signal S is sampled at predetermined sampling intervals, and the sampled image signal is digitized into a digital image signal Sd1. In the first radiation image read-out apparatus 31, the analog output signal S is sampled by the A/D converter 28 at sampling intervals of $\Delta x=1/(2 \cdot fss)=0.2$ (mm), i.e. is sampled five times per mm. Also, no operation for eliminating the grid image 6 is carried out. Therefore, it often occurs that the image signal Sd1 contains the signal components, which represents the grid image 6. A code, which represents that the image signal has been obtained with the first radiation image read-out apparatus 31, is added to the image signal Sd1. Thereafter, the image signal Sd1 is fed into a compressor 33 and subjected to a compressing process which will be described later. An image signal Sd1' obtained from the compressing process is stored on a storage medium of an image filing device 34, such as an optical disk unit.

The second radiation image read-out apparatus 32 shown in FIG. 1 has the same basic structure as that of the first radiation image read-out apparatus 31. A digital image signal (an original image signal) Sd2 is obtained from the second radiation image read-out apparatus 32.

Figure 5:
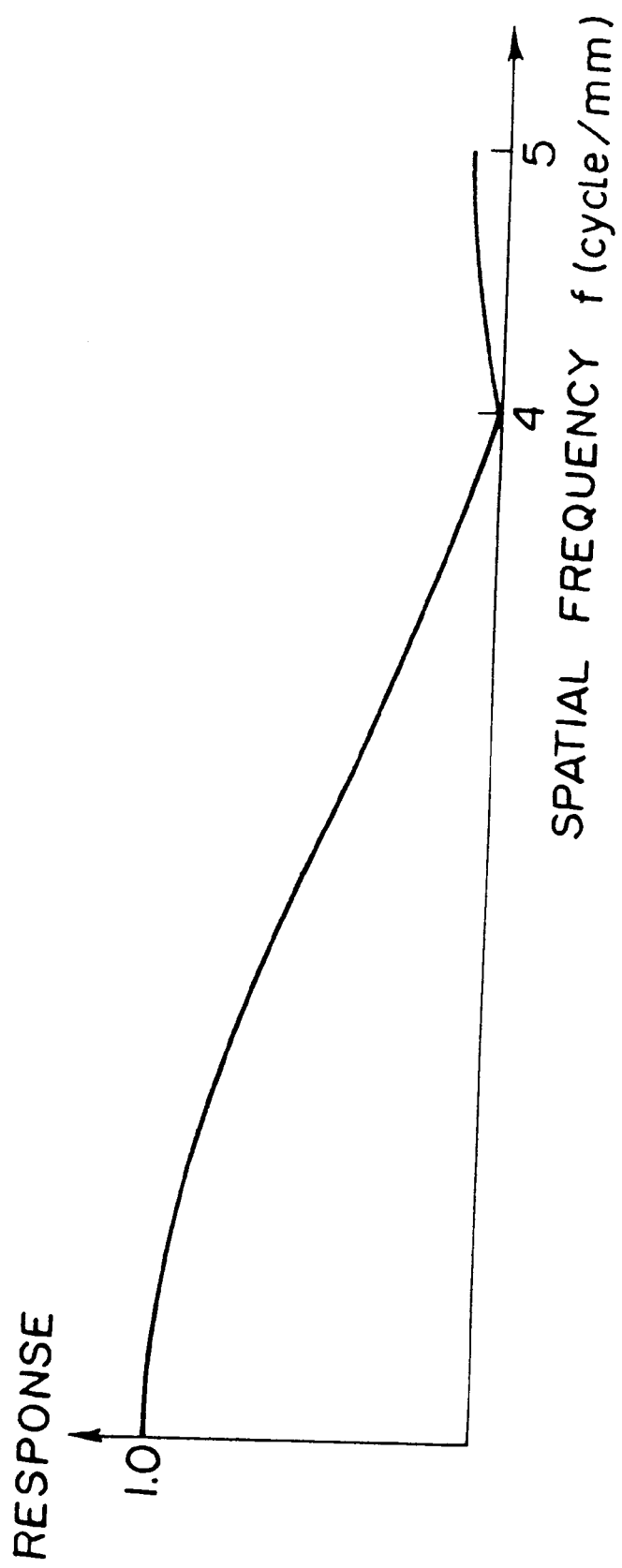
FIG. 5 is a graph showing characteristics of filtering processing for eliminating a grid image.
Figure 6A:
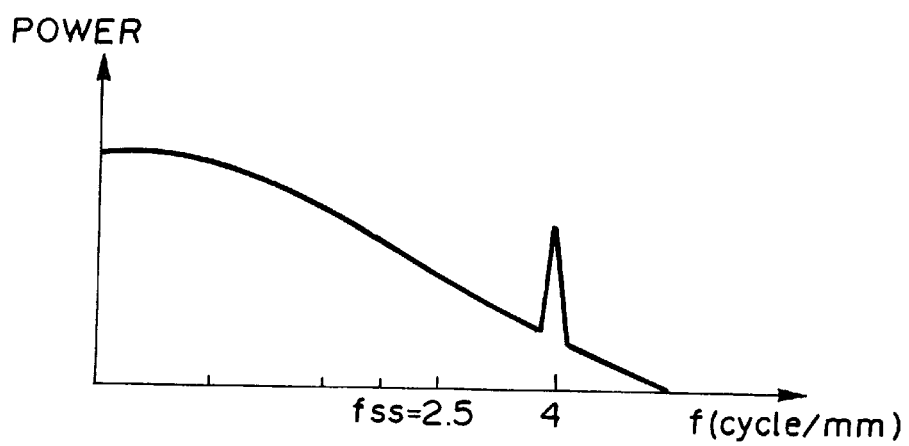
FIGS. 6A, 6B, and 6C are graphs showing spatial frequency characteristics of a radiation image which comprises an object image and a striped grid image superposed upon the object image.
Figure 6B:
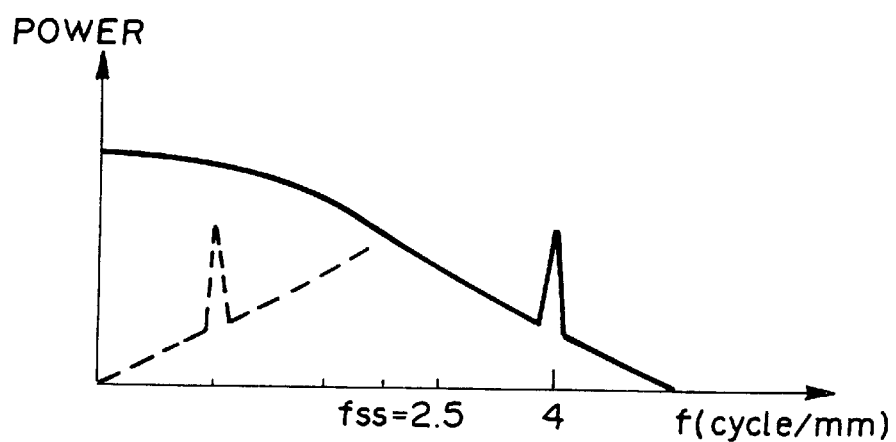
Figure 6C:
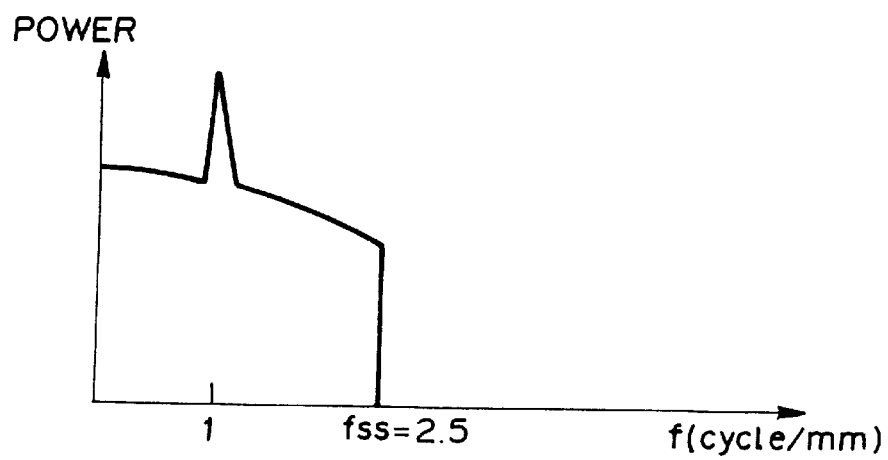

In the second radiation image read-out apparatus 32, an analog output signal S is sampled by the A/D converter 28 at sampling intervals of $\Delta x=0.1$ (mm), i.e. is sampled ten times per mm. The digital image signal (the original image signal) Sd2 obtained from the A/D converter 28 is stored in a storage means 41. The image signal Sd2 is then read from the storage means 41 and is fed into an image signal generating means 42. In the image signal generating means 42, the image signal Sd2 is subjected to filtering processing for eliminating the signal components corresponding to the spatial frequency of 4 cycles/mm of the grid image 6. FIG. 5 shows the characteristics of the filtering processing. The image signal Sd2, which has been obtained from the filtering processing, is then resampled in the image signal generating means 42. During the resampling processing, the image signal Sd2 is sampled at sampling intervals of $\Delta x=0.2$ (mm), i.e. is sampled five times per mm.

The filtering processing and the resampling processing are described in detail in Japanese Unexamined Patent Publication No. 3(1991)-114039. In cases where the filtering processing and the resampling processing are carried out, even if the original image signal Sd2 is the one which has been detected from a stimulable phosphor sheet 11 having the radiation image stored thereon by using the grid 4, basically, a digital image signal Sd2' obtained from the filtering processing and the resampling processing will not contain the components representing the grid image 6. A code, which represents that the image signal has been subjected to the processing by the image signal generating means 42, is added to the image signal Sd2'. Thereafter, the image signal Sd2' is stored in the storage means 41 and is then fed from the storage means 41 into the compressor 33. An image signal Sd2' having been compressed by the compressor 33 is stored on the storage medium in the image filing device 34.

The image signals Sd1' and Sd2' are then read from the storage medium of the image filing device 34 and fed into a decompressor 35, which carries out predetermined decompression processing on the image signals Sd1' and Sd2'. A decompressed image signal Se1 is obtained from the decompression processing carried out on the image signal Sd1'. Also, a decompressed image signal Se2 is obtained from the decompression processing carried out on the image signal Sd2'. The decompressed image signals Se1 and Se2 are fed into an image reproducing apparatus 36, which may be constituted of a CRT display device, a light beam scanning recording apparatus, or the like. The image reproducing apparatus 36 reproduces visible radiation images from the decompressed image signals Se1 and Se2.

How the compressor 33 carries out the compressing processes will be described hereinbelow. As for the image signal Sd1 assigned with the code which represents that the image signal has been obtained from the first radiation image read-out apparatus 31, the compressor 33 carries out the compressing process capable of restricting the occurrence of a moire. As for the digital image signal Sd2' assigned with the code which represents that the image signal has been subjected to the processing by the image signal generating means 42, the compressor 33 carries out the compressing process which is advantageous with respect to the compression processing speed, the compressibility, and the image quality (the sharpness).

Figure 8:
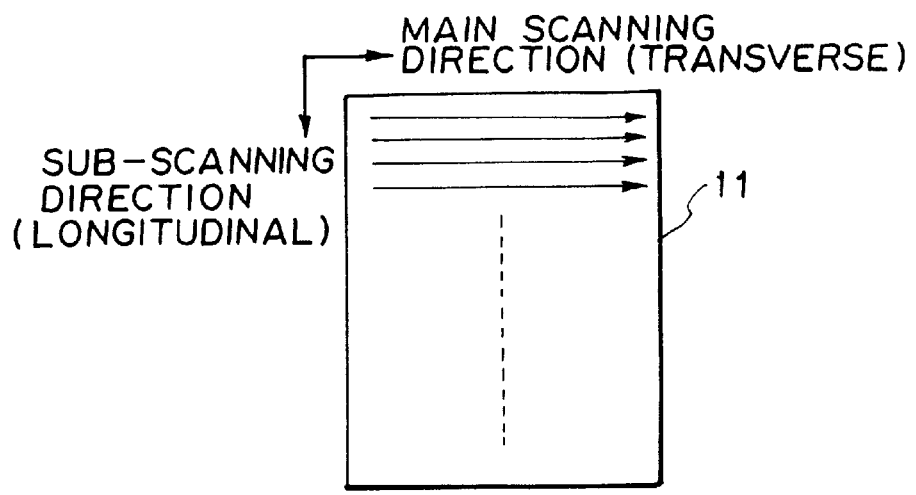
FIG. 8 is a schematic view showing how an image signal is detected from a stimulable phosphor sheet on which an image has been recorded.

First, how the compressing process is carried out on the image signal Sd1 will be described hereinbelow with reference to FIG. 7. The compressing process is described in U.S. Pat. No. 5,086,489. In this embodiment, the digital image signal (i.e. the original image signal) Sd1 is made up of a series of image signal components representing 2,000×2,000 picture elements, and each image signal component representing one picture element comprises an information amount of 8 bits (0 to 255 levels of density). FIG. 8 shows the directions, in which the stimulable phosphor sheet 11 is scanned with the laser beam 17. The position of each picture element with respect to the sub-scanning direction is represented by "i," and the position of each picture element with respect to the main scanning direction is represented by "j." The original image signal components representing the respective picture elements are represented by Aij.

First, original image signal components Aij are subjected to the component number decreasing processing with which the number of the original image signal components Aij is decreased. During the component number decreasing processing, the phase shift sampling is carried out wherein the phase of the sampling is varied between sampling lines.

Figure 9:
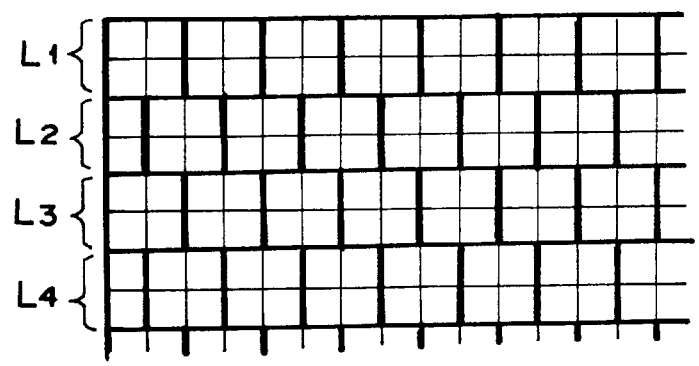
FIG. 9 is an explanatory view showing how the component number decreasing processing (phase shift sampling) is carried out in the image signal compressing process of FIG. 7.

FIG. 9 is an explanatory view showing how the phase shift sampling is carried out in this embodiment. In FIG. 9, each of the small squares represents a single picture element in an image.

With reference to FIG. 9, a mean reduction sampling process is employed. With the mean reduction sampling process, a single representative image signal component is sampled from the image signal components corresponding to each block, which comprises 2×2 picture elements, and the number of the original image signal components is decreased to one fourth. Also, the mean value of the values of the image signal components representing the four picture elements in each block is employed as the value of the representative image signal component. First, as illustrated in FIG. 9, a plurality of block lines L1, L2, L3, L4, . . . are set in parallel along the main scanning direction on the image. The width of each line, which width is taken in the sub-scanning direction, corresponds to the total width of two picture elements. A plurality of blocks, each of which comprises 2×2 picture elements, are set continuously along each block line such that the phases of the blocks located along a block line are shifted by one half of the length of a single block (i.e. a distance equal to the length of a single picture element) from the phases of the blocks located along a neighboring block line. Then, the mean value of the image signal components representing the picture elements in each block is calculated and determined as the value of the representative image signal component (the mean reduced component). Only the representative image signal components thus determined for the respective blocks are sampled as new image signal components.

Figure 10:
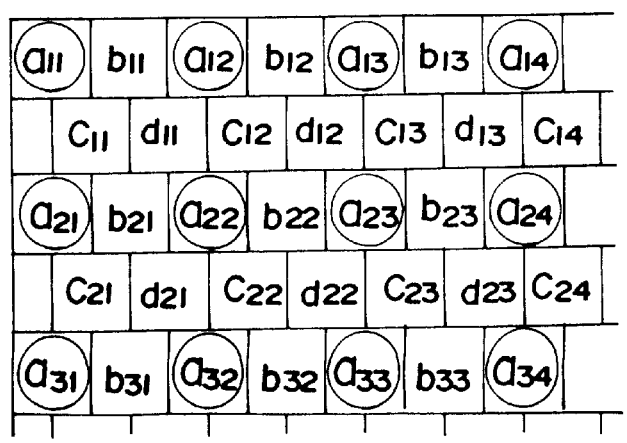
FIG. 10 is an explanatory view showing how the main components are sampled.

FIG. 10 shows the representative image signal components obtained from the aforesaid phase shift sampling. In FIG. 10, each square represents a single block comprising 2×2 picture elements, and aij, bij, cij, and dij indicated in the squares denote the representative image signal components corresponding to the respective blocks.

Thereafter, the interpolation encoding is carried out in the manner described below on the representative image signal components obtained from the aforesaid phase shift sampling. First, the representative image signal components are classified into main components, which have been sampled at appropriate sampling intervals, and interpolated components other than the main components. In this embodiment, the main components are sampled at sampling intervals of two blocks along the transverse and longitudinal directions of the arrangement of the blocks. Therefore, in FIG. 10, the representative image signal components aij indicated by circles are sampled as the main components, and the other representative image signal components bij, cij, and dij are taken as the interpolated components.

Thereafter, a quantization process is carried out on the main components aij such that the density resolution is made coarser by 1 bit. Specifically, each of the main components aij is shifted by 1 bit toward the low order side, and the least significant bit is omitted. From the quantization, quantized main components aij' are obtained.

The quantized main components aij' corresponding to each block line are then subjected to the previous value prediction and converted into prediction errors $\Delta aij$. However, the quantized main components aij' (j=1) corresponding to the blocks at the tops of the respective block lines remain unconverted. FIG. 11 shows the prediction errors $\Delta aij$ obtained from the previous value prediction. The previous value prediction errors $\Delta aij$ are represented by the formula $$\Delta a_{ij}=a_{ij}'-a_{ij-1}'$$

Specifically, they are represented by the formulas $\Delta a_{12}=a_{12}'-a_{11}'$, $\Delta a_{13}=a_{13}'-a_{12}'$, ...
$\Delta a_{22}=a_{22}'-a_{21}'$, $\Delta a_{23}=a_{23}'-a_{22}'$, ...
$\Delta a_{32}=a_{32}'-a_{31}'$, $\Delta a_{33}=a_{33}'-a_{32}'$, ...

Thereafter, the previous value prediction errors $\Delta aij$ are encoded into Huffman codes. Table 1 shows an example of the Huffman code table used for this purpose.

TABLE 1

| Data to be encoded | Length of code | Huffman code |
| --- | --- | --- |
| −7 | 10 | 0000000001 |
| −6 | 9 | 000000001 |
| −5 | 8 | 00000001 |
| −4 | 7 | 0000010 |
| −3 | 7 | 0000011 |
| −2 | 6 | 000011 |
| −1 | 3 | 001 |
| 0 | 1 | 1 |
| 1 | 2 | 01 |
| 2 | 4 | 0001 |
| 3 | 7 | 0000101 |
| 4 | 8 | 00001000 |
| 5 | 9 | 000010010 |
| 6 | 10 | 0000100111 |
| 7 | 10 | 0000100110 |
| ext | 7 | 0000001 |

Specifically, the previous value prediction errors $\Delta aij$, which are the objects of the encoding, are converted into the Huffman codes in accordance with the Huffman code table shown in Table 1. However, in cases where the previous value prediction errors $\Delta aij$ go beyond the range between predetermined threshold values (±7 in the Huffman code table shown in Table 1), they are converted into the format in which they follow the extension (EXT) code, i.e. are encoded into the form of 0000001+previous value prediction errors $\Delta aij$.

When the main components compressed in the manner described above are stored on the storage medium in the image filing device 34, the signal components corresponding to the tops of the respective block lines (TOL: TOP OF LINE) are stored in the format of the quantized main components aij' (j=1). The signal components corresponding to the other blocks are stored in the format of the Huffman codes, into which the components have been encoded in accordance with the Huffman code table shown above, and in the format of EXT code+previous value prediction errors $\Delta aij$.

Processing carried out on the interpolated components bij, cij, and dij shown in FIG. 10 will be described hereinbelow. First, the interpolation prediction from the main components is carried out on the interpolated components bij, cij, and dij, and interpolation prediction errors $\Delta bij$, $\Delta cij$, and $\Delta dij$ are obtained. The interpolation prediction may be carried out in one of various manners. In this embodiment, the quantized main components aij' are used as the main components. Also, the interpolation prediction errors $\Delta bij$, $\Delta cij$, and $\Delta dij$ are calculated from the interpolation prediction formulas expressed as $$\Delta b_{11}=b_{11}-(a_{11}'\times 2+a_{12}'\times 2)/2$$

$$c_{11}=c_{11}-(a_{11}'\times 2\times 3+a_{12}'\times 2) +a_{21}'\times 2\times 3+a_{22}'\times 2)/8$$

$$\Delta d_{11}=d_{11}-(a_{11}'\times 2+a_{12}'\times 2\times 3+a_{21}'\times 2+a_{22}'\times 2\times 3)/8$$

The relationship between the positions of a11', a12', a21', and a22' and the positions of $\Delta b11$, $\Delta c11$, and $\Delta d11$ is shown in FIG. 12. The interpolation prediction errors corresponding to the other interpolated components can be calculated from the similar formulas.

Thereafter, interpolation prediction errors $\Delta bij$, $\Delta cij$, and $\Delta dij$ corresponding to the interpolated components are quantized such that the bit resolution is made coarser by 1 bit. During the quantization, the quantization characteristics A shown in Table 2 and the quantization characteristics B shown in Table 3 are utilized. The quantization characteristics A are applied to the interpolation prediction errors $\Delta bij$ corresponding to the interpolated components bij. The quantization characteristics B are applied to the interpolation prediction errors $\Delta cij$ and $\Delta dij$ corresponding to the interpolated components cij and dij.

TABLE 2

(Quantization characteristics A)

| Prediction errors | After quantization | After decompression |
| --- | --- | --- |
| −255 | −128 | −256 |
| −254 | −127 | −254 |
| . | . | . |
| . | . | . |
| . | . | . |
| −3 | −2 | −4 |
| −2 | −1 | −2 |
| −1 | −1 | −2 |
| 0 | 0 | 0 |
| 1 | 0 | 0 |
| 2 | 1 | 2 |
| 3 | 1 | 2 |
| . | . | . |
| . | . | . |

TABLE 2-continued (Quantization characteristics A)

| Prediction errors | After quantization | After decompression |
| --- | --- | --- |
| . | . | . |
| . | . | . |
| . | . | . |
| 254 | 127 | 254 |
| 255 | 127 | 254 |

TABLE 3

(Quantization characteristics B)

| Prediction errors | After quantization | After decompression |
| --- | --- | --- |
| −256 | −127 | −255 |
| −255 | −127 | −255 |
| . | . | . |
| . | . | . |
| . | . | . |
| −3 | −1 | −3 |
| −2 | −1 | −3 |
| −1 | 0 | −1 |
| 0 | 0 | −1 |
| 1 | 1 | 1 |
| 2 | 1 | 1 |
| 3 | 2 | 3 |
| . | . | . |
| . | . | . |
| . | . | . |
| 254 | 127 | 253 |
| 255 | 127 | 255 |

The quantized interpolation prediction errors Δbij', Δcij', and Δdij' thus obtained are then encoded into Huffman codes. As in the case of the encoding of the main components into Huffman codes, the Huffman code table shown in Table 1 is used for this purpose. Specifically, the quantized interpolation prediction errors Δbij', Δcij', and Δdij', which are the objects of the encoding, are converted into the Huffman codes in accordance with the Huffman code table shown in Table 1. In cases where the quantized interpolation prediction errors Δbij', Δcij', and Δdij' go beyond the range between the predetermined threshold values ±7, they are converted into the format in which they follow the extension (EXT) code, 0000001.

When the interpolated components, which have been compressed in the manner described above, are stored on the storage medium in the image filing device 34, they are stored in the format of the Huffman codes, into which they have been encoded in accordance with the Huffman code table shown above, and in the format of EXT code+quantized interpolation prediction errors Δbij', Δcij', and Δdij'.

Figure 13:
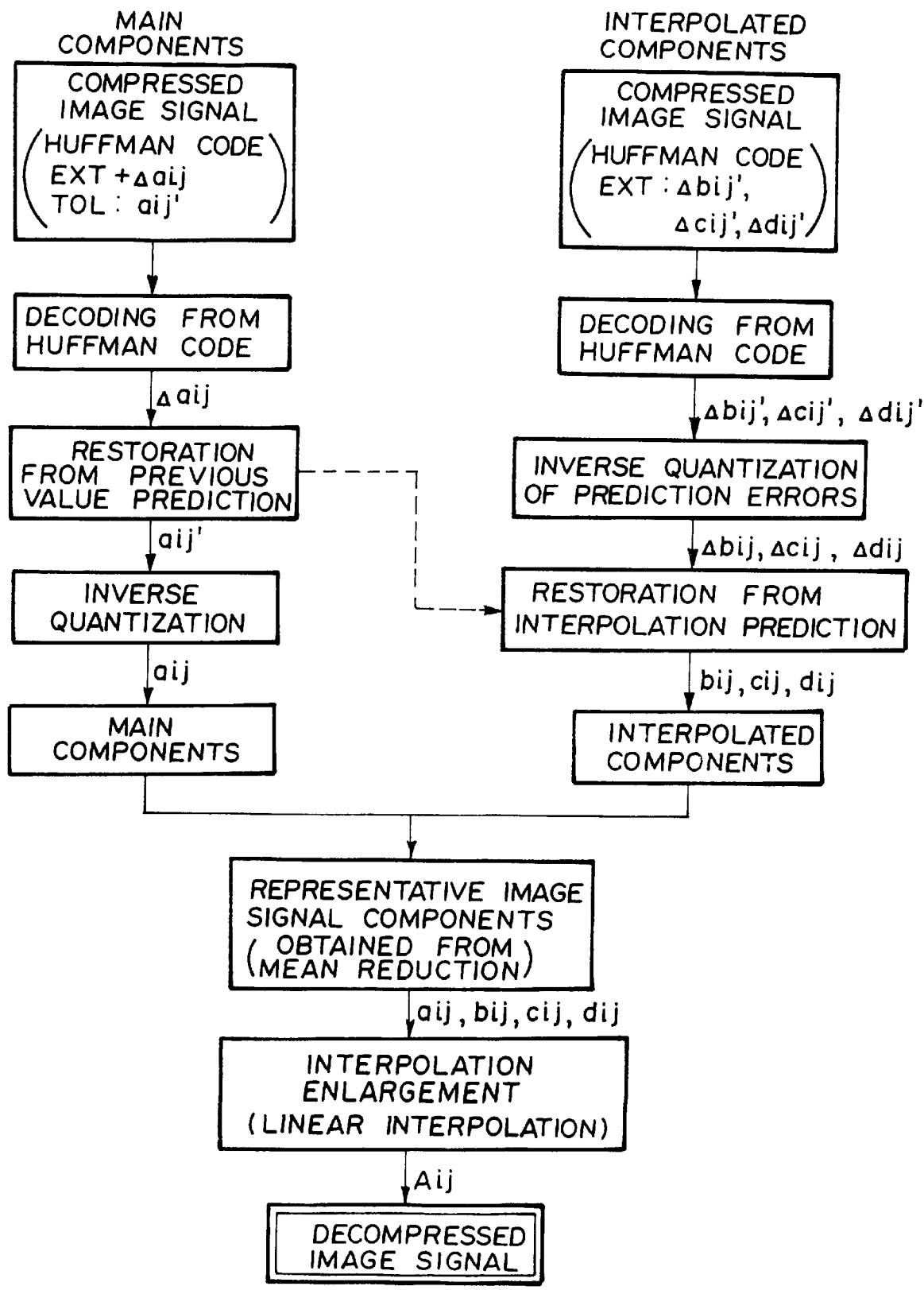
FIG. 13 is a flow chart showing how an image signal, which has been compressed with the process of FIG. 7, is decompressed.

How the decompression processing is carried out by the decompressor 35 on the compressed image signal Sd1', which has been read from the storage medium of the image filing device 34, will be described hereinbelow. In the aforesaid compressor 33, the code, which represents that the image signal has been subjected to the compressing process described above, has been added to the compressed image signal Sd1'. As for the compressed image signal Sd1' assigned with this code, the decompressor 35 carries out the decompression processing described below. FIG. 13 is a flow chart showing the decompression processing. The steps of the decompression processing are reverse to the steps of the compressing process shown in FIG. 7.

Figure 14:
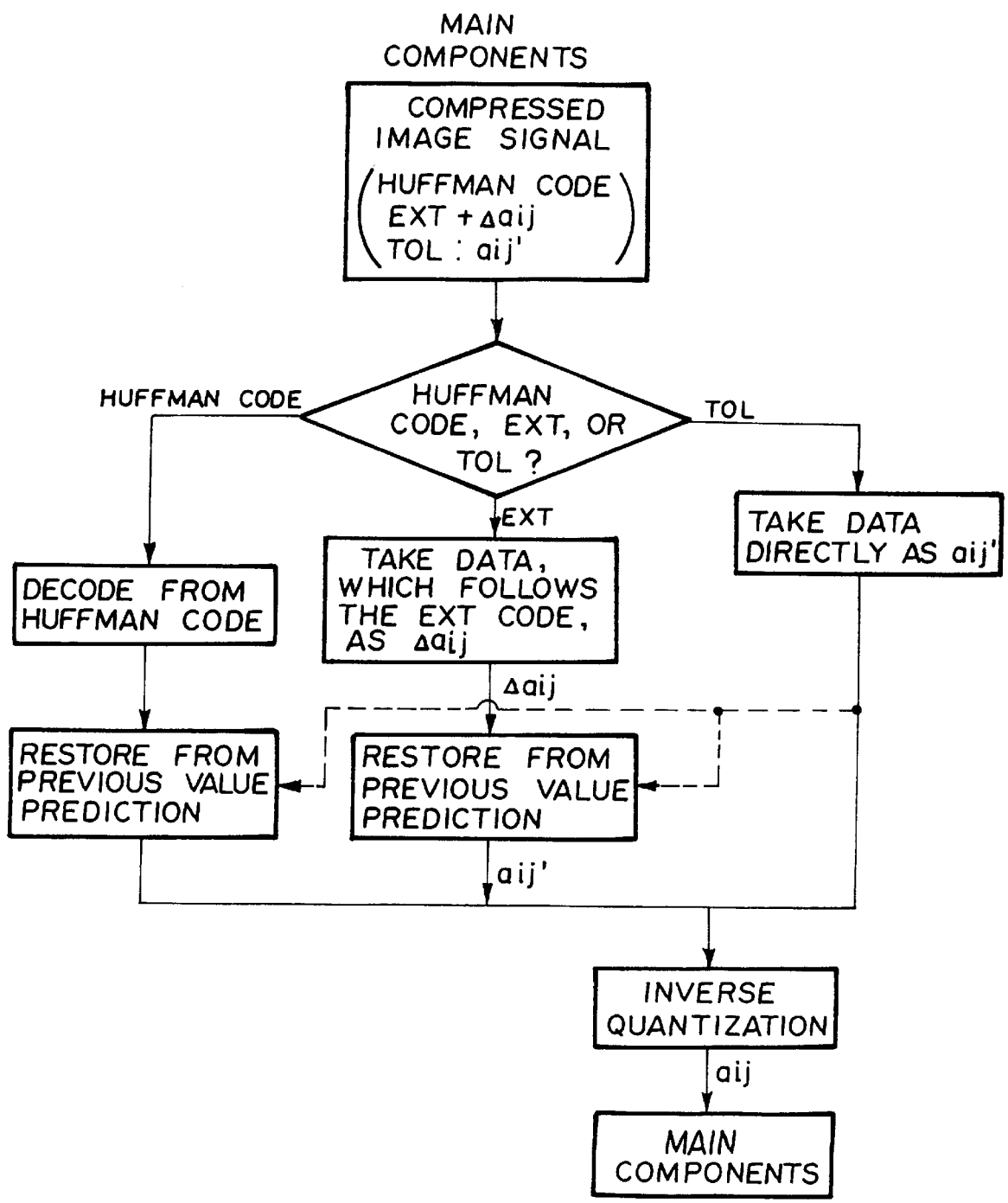
FIG. 14 is a flow chart showing part of the flow chart of FIG. 13, which part is related to the main components.

First, how the compressed main components are decompressed will be described hereinbelow with reference to FIG. 14. As described above, the compressed main components are stored in the three formats: the Huffman codes, the EXT code+quantized previous value prediction errors Δaij, and the quantized main components aij' corresponding to the TOL blocks. Therefore, a judgment is made as to which format the compressed main components read from the storage medium of the image filing device 34 have. In cases where the compressed main components read from the storage medium of the image filing device 34 are those corresponding to the TOL blocks, they are directly taken as the quantized main components aij'.

In cases where the compressed main components read from the storage medium of the image filing device 34 are the Huffman codes, they are decoded in accordance with the Huffman code table shown in Table 1 into the previous value prediction errors Δaij. Thereafter, the restoration from the previous value prediction is carried out on the previous value prediction errors Δaij, the quantized main components aij' (j=1) corresponding to the TOL blocks, and the quantized main components aij' obtained from the EXT code+previous value prediction errors Δaij. In this manner, the quantized main components aij' are restored. The restoration from the previous value prediction is carried out with the formula $$a_{ij}' = a_{ij-1}' + \Delta a_{ij}$$

Specifically, because the quantized main components aij' (j=1) corresponding to the TOL blocks have already been obtained, the formulas expressed as $$a_{12}' = a_{11}' + \Delta a_{12}, \ a_{13}' = a_{12}' + \Delta a_{13}, \ldots$$
$$a_{22}' = a_{21}' + \Delta a_{22}, \ a_{23}' = a_{22}' + \Delta a_{23}, \ldots$$
$$a_{32}' = a_{31}' + \Delta a_{32}, \ a_{33}' = a_{32}' + \Delta a_{33}, \ldots$$

are used.

In cases where the compressed main components read from the storage medium are the EXT code+previous value prediction errors Δaij, in the same manner as that for the Huffman codes, the quantized main components aij' are restored from the previous value prediction errors Δaij which follow the EXT code.

In the manner described above, the quantized main components aij' are restored for all image signal components of the compressed image signal Sd1'. Thereafter, the quantized main components aij' are subjected to inverse quantization, i.e. are shifted by 1 bit to the high order side. In this manner, the main components aij (the representative image signal components) are obtained.

Figure 15:
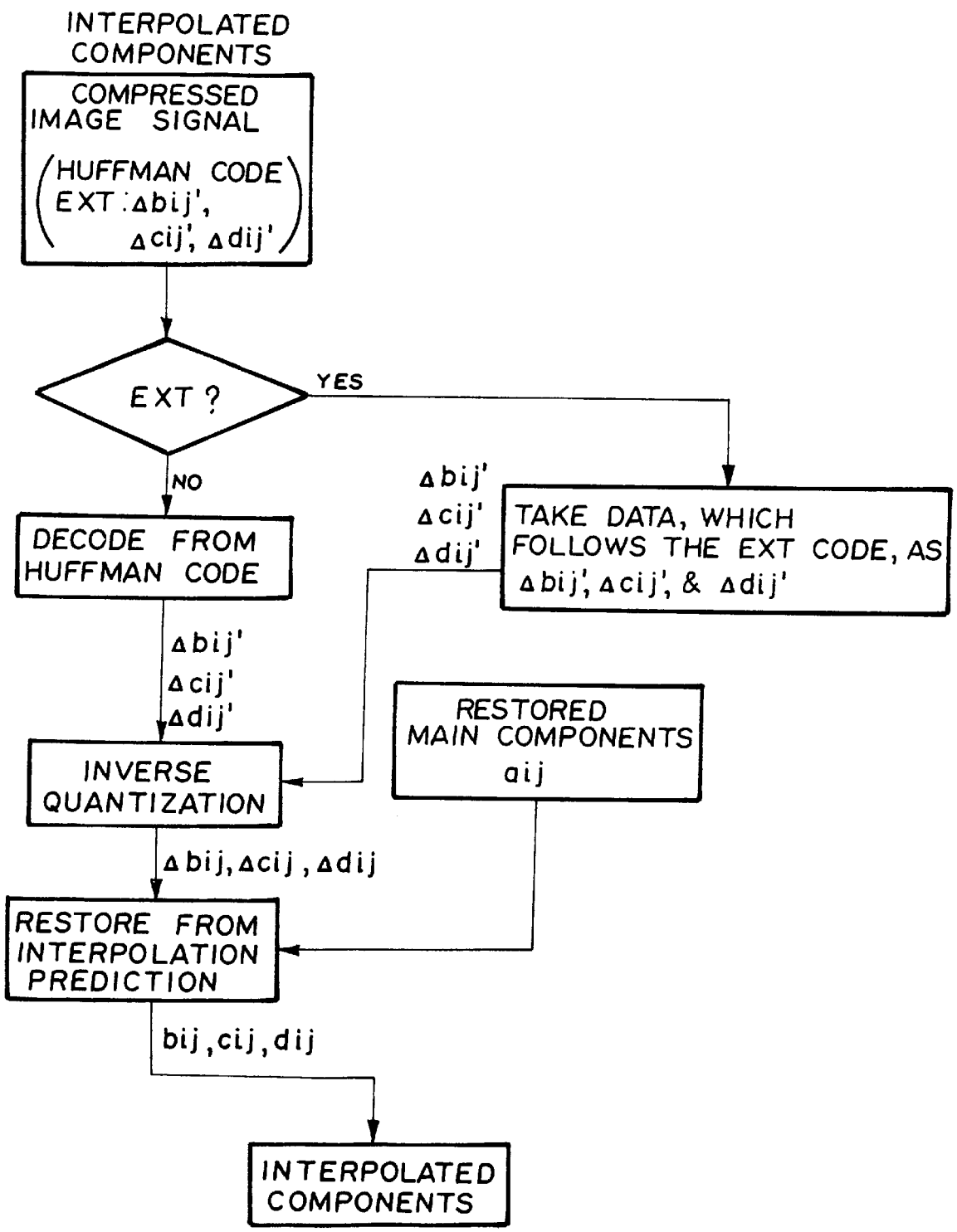
FIG. 15 is a flow chart showing part of the flow chart of FIG. 13, which part is related to the interpolated components.

How the interpolated components which have been compressed are decompressed will be described hereinbelow with reference to FIG. 15.

As described above, the interpolated components, which have been compressed, are stored in the two formats: the Huffman codes, and the EXT code+quantized interpolation prediction errors Δbij', Δcij', and Δdij'. Therefore, a judgment is made as to which format the compressed image signal components read from the storage medium of image filing device 34 have. In cases where the compressed image signal components read from the storage medium are the Huffman codes, they are decoded in accordance with the Huffman code table shown in Table 1 into the quantized interpolation prediction errors Δbij', Δcij', and Δdij'. Thereafter, the quantized interpolation prediction errors obtained from the decoding are subjected to the inverse quantization, from which the interpolation prediction errors Δbij, Δcij, and Δdij are obtained. The restoration from the interpolation prediction is then carried out on the interpolation prediction errors Δbij, Δcij, and Δdij and the main components aij which have already been obtained during the restoration from the previous value prediction. In this manner, the interpolated components (the representative image signal components) bij, cij, and dij are restored. The restoration from the interpolation prediction is carried out with the formulas $$b_{11}=\Delta b_{11}+(a_{11}+a_{12})/2$$

$$c_{11}=\Delta c_{11}+(a_{11}\times 3+a_{12}+a_{21}\times 3+a_{22})/8$$

$$d_{11}=\Delta d_{11}+(a_{11}+a_{12}\times 3+a_{21}+a_{22}\times 3)/8$$

The other 8-bit interpolated components bij, cij, and dij are restored from similar formulas. In cases where the compressed image signal components read from the storage medium are the EXT code+quantized interpolation prediction errors Δbij', Δcij', and Δdij', in the same manner as that for the Huffman codes, the interpolated components bij, cij, and dij are restored from the quantized interpolation prediction errors Δbij', Δcij', and Δdij' which follow the EXT code.

In the manner described above, all of the representative image signal components aij, bij, cij, and dij comprising the main components and the interpolated components are restored. Thereafter, as shown in FIG. 13, interpolation enlargement is carried out on the representative image signal components aij, bij, cij, and dij such that the number of the image signal components is increased to four times as large as the number of the representative image signal components aij, bij, cij, and dij. In this manner, the decompressed image signal components Aij corresponding to the original image signal are restored. The decompressed image signal Se1, which is made up of a series of the decompressed image signal components Aij, is fed into the image reproducing apparatus 36 and used during the reproduction of the radiation image.

How the interpolation enlargement (restoring interpolation) is carried out on the representative image signal components aij, bij, cij, and dij will be described hereinbelow with reference to FIG. 16. In FIG. 16, each square represents a single picture element. By way of example, as illustrated, the representative image signal components aij, bij, cij, and dij which has been restored are set as the decompressed image signal components Aij representing the left, upper picture elements of the corresponding blocks. From the decompressed image signal components Aij thus set, the other decompressed image signal components Aij are restored. For this purpose, the linear interpolation is carried out along the main scanning direction and the sub-scanning direction. For example, the decompressed image signal components A12, A22, A23, and A33 are restored with the formulas $$A_{12}=(a_{11}+b_{11})/2$$

$$A_{22}=(A_{12}+c_{11})/2=\{(a_{11}+b_{11})/2+c_{11}\}/2$$

$$A_{33}=(c_{11}+d_{11})/2$$

$$A_{23}=(b_{11}+A_{33y})2=\{b_{11}+(c_{11}+d_{11})/2\}/2$$

The other decompressed image signal components Aij can be restored in the same manner as th at described above.

In the aforesaid embodiment, smoothing processing may be carried out before the component number decreasing processing. As one of the smoothing processing techniques, for example, moving average filter processing may be employed. With the moving average filter processing, a mask having a size corresponding to, for example, 3×3 picture elements is prepared. The mask is located so that its center may coincide with a remark picture element. The mean value of the values of the image signal components representing the nine picture elements included in the mask is taken as the value of a new image signal component corresponding to the remark picture element. Such processing is carried out for every picture element. With the smoothing processing, the correlation between the image signal components representing the neighboring picture elements can be improved. As a result, the extent of concentration of prediction errors, which occur during the previous value prediction and the interpolation prediction, at values near zero can be made high, and the signal compressibility can be kept high.

In cases where the interpolation encoding processing is carried out after the component number decreasing processing is carried out with the phase shift sampling, wherein the phases of the sampling points along a sampling line are shifted from the phases of the sampling points along a neighboring sampling line, the image signal compressibility can be kept higher than when the interpolation encoding processing is carried out after the component number decreasing processing is carried out with the in-phase sampling, in which the phases of the sampling points along a sampling line are not shifted from those along a neighboring sampling line. This is presumably because, when the values of the interpolated components are predicted with the interpolation prediction from the main components, which have been sampled with the phase shift sampling, a higher accuracy of prediction of the values of the interpolated components can be achieved than when the interpolation prediction is carried out from the main components, which have been sampled with the in-phase sampling.

As described above, the signal compressibility can be increased when the component number decreasing processing, in which the phase shift sampling is utilized, is employed. Also, when the phase shift sampling is employed, the coarseness of a visible image reproduced from an image signal restored from the compressed image signal can be kept visually less perceptible, and the apparent sharpness of the visible image can be kept higher than when the in-phase sampling is employed. Additionally, in cases where the image signal Sd1 is the one which has been detected from the stimulable phosphor sheet 11 carrying the radiation image stored thereon by using the grid 4, a moire can be prevented from occurring on the reproduced radiation image.

In the aforesaid embodiment, each block comprises 2×2 picture elements. However, each block may be composed of n×n picture elements, where n≧3. Also, instead of the mean value of the values of the image signal components corresponding to each block being set as the representative image signal component for the block, the value of an image signal component representing a picture element located at a specific position in each block may be employed as the representative image signal component for the block.

Also, in the aforesaid embodiment, the main components are subjected to the quantization and the combination of the previous value prediction with the encoding into the Huffman codes. Alternatively, the main components may not be subjected to any particular processing. As another alternative, the main components may be subjected to other appropriate types of processing. The quantization may be carried out in any of various other manners. Also, the prediction errors found during the previous value prediction may be quantized.

In the embodiment described above, the quantization of the interpolation prediction errors is carried out for the interpolated components. Alternatively, this quantization step may be omitted or may be carried out in one of other ways. As another alternative, the interpolated components themselves may be subjected to the quantization. Also, the interpolation prediction may be carried out in a different manner (with other interpolation prediction formulas). Any of code tables other than the Huffman code table may be used during the encoding of the interpolation prediction errors.

How the compressing process is carried out on the image signal Sd2' will be described hereinbelow. The compressing process employed for the image signal Sd2' is described in U.S. Pat. No. 4,941,194. FIG. 17A is a process flow chart showing how the compressing process is carried out. As illustrated in FIG. 17A, pre-processing for decreasing the number of image signal components is carried out on the original image signal Sd2'. Thereafter, redundancy suppression encoding processing is carried out on the image signal whose image signal components have been decreased by the pre-processing. A compressed signal, which has been encoded by the redundancy suppression encoding processing, is stored on a storage medium, such as an optical disk, in the image filing device 34.

As shown in the decompression processing flow chart of FIG. 17B, when the radiation image is to be reproduced from the image signal which has thus been compressed and stored, the compressed image signal Sd2" is first read from the storage medium of the image filing device 34 and decoded in accordance with the encoding table, which was used in the aforesaid redundancy suppression encoding processing. Also, the component number restoring post-processing is conducted based on the decoded image signal. Specifically, some image signal components are calculated and restored based on the decoded image signal so that the number of the image signal components may become equal to the number of the image signal components which were present prior to the component number decreasing pre-processing. Thereafter, the image signal, which has thus restored, is fed into the image reproducing apparatus 36. (Of course, the restored image signal includes the image signal components, which have been restored by the component number restoring post-processing, and the image signal components, which have been restored by the aforesaid decoding processing.)

Figure 18A:
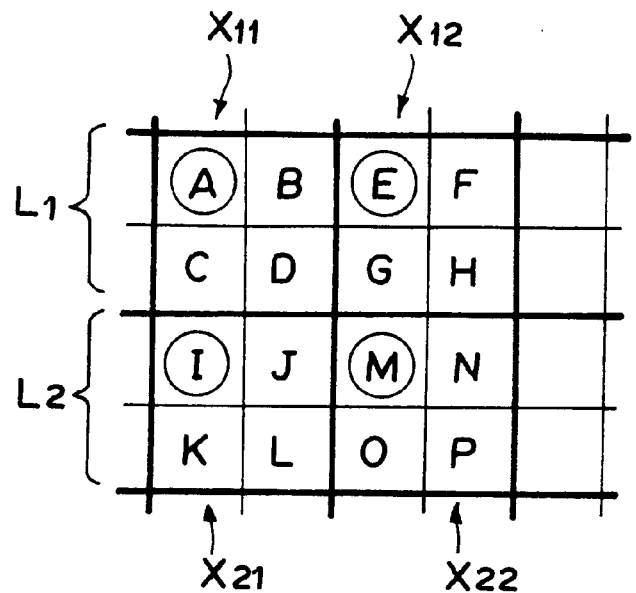
FIG. 18A is an explanatory view showing an example of component number decreasing pre-processing employed in the image signal compressing process shown in FIG. 17A.

In short, the aforesaid component number decreasing pre-processing is carried out in order to decrease the number of the image signal components, which are to be recorded, and may be carried out by one of various processing methods. FIG. 18A shows an example of the component number decreasing pre-processing. In FIG. 18A, each cell represents a single picture element of a radiation image, and the characters A, B, C, . . . in the respective cells represent the image signal components (the original image signal components) representing the respective picture elements.

In this example, as shown in FIG. 18A, the radiation image is divided into blocks, each of which is composed of 2×2 picture elements. Image signal components A, E, . . . , I, M, . . . representing the picture elements, which are located at predetermined positions (in this example, the left top positions indicated by circles in FIG. 18A) in the respective blocks (i.e. the cells surrounded by bold lines) X11, X12, . . . , X21, X22, are taken as representative image signal components a11, a12, . . . , a21, a22, . . . (a11=A, a12=E, a21=I, a22=M, . . . ) of the respective blocks X11, X12, . . . , X21, X22, . . . Only the representative image signal components are sampled as the image signal components which are to be recorded. With this method, it is possible to decrease the number of the image signal components to one fourth.

Thereafter, the redundancy suppression encoding processing is carried out on the thus decreased image signal components a11, a12, . . . , a21, a22, . . . in the manner described above. In short, the redundancy suppression encoding processing is the processing for encoding by suppressing the redundancy of information which the image signal components carry. The redundancy suppression encoding processing typically includes prediction encoding, encoding by orthogonal transformation, or the like.

In this example, prediction encoding is carried out by use of previous value prediction and Huffman codes in the manner which will be described below. The representative image signal components a11, a12, . . . , a21, a22, . . . , which have been obtained for the respective blocks from the component number decreasing pre-processing, are arrayed as shown in FIG. 19. The cells in FIG. 19 correspond to the respective blocks X11, X12, . . . , X21, X22, . . . shown in FIG. 18A.

First, the respective image signal components are subjected to previous value prediction, and differences between the predicted values and the actual values of the image signal components, i.e. prediction errors, are calculated. Specifically, the line of the blocks X11, X12, X13, . . . which have the representative image signal components a11, a12, a13, . . . , is taken as a first block line L1. The line of the blocks, which have the representative image signal components a21, a22, a23, . . . , is taken as a second block line L2. Also, the line of the blocks, which have the representative image signal components a31, a32, a33, . . . , is taken as a third block line L3. The representative image signal components a11, a21 and a31 are assumed respectively to be the representative image signal components of the head blocks on the block lines L1, L2 and L3. In this case, on the first block line L1, the signal value a11 is left as it is, and a12 is predicted to be equal to the previous signal value a11. A calculation is made to find a prediction error $\Delta a12 = a12 - a11$ between the actual signal value a12 and the predicted signal value a11. Also, the signal value a13 is predicted to be equal to the previous signal value a12, and a calculation is made to find a prediction error $\Delta a13 = a13 - a12$ between the actual signal value a13 and the predicted signal value a12. In the same manner as that described above, $\Delta a14, \Delta a15, \ldots$ are calculated. Also, as for the second block line L2, in the same manner as that described above, the head signal value a21 is left as it is, and prediction errors $\Delta a22, \Delta a23, \Delta a24, \ldots$ are calculated for a22, a23, a24, . . . Further, as for the third block line L3, in the same manner as that described above, the head signal value a31 is left as it is, and prediction errors $\Delta a32, \Delta a33, \Delta a34, \ldots$ are calculated for a32, a33, a34, . . .

In the manner described above, as illustrated in FIG. 20, a11, $\Delta a12, \Delta a13, \ldots$ , a21, $\Delta a22, \Delta a23, \ldots$ , and a31, $\Delta a32, \Delta a33, \ldots$ are obtained. Thereafter, they are encoded into Huffman codes.

In general, an image signal component (a remark image signal component) attains a signal value, which is not so much different from the signal value of a neighboring image signal component. Specifically, it may be considered that there is not a large difference between the value of the remark image signal component and the value of the neighboring image signal component. Therefore, the value of the remark image signal component may be predicted to be equal to the value of the neighboring image signal component (in the aforesaid case, the image signal component, which is located prior to the remark image signal component), and the error of the prediction ($\Delta a21, \Delta a22$, or the like) may be calculated. In such cases, distribution of the prediction errors is concentrated in the vicinity of zero. The prediction error encoding utilizes the characteristics that the prediction errors are concentrated to the vicinity of zero. With the prediction error encoding, the prediction errors and the image signal components a11, a21, a31, . . . located at the head blocks on the respective block lines are encoded into Huffman codes such that a shorter code may be allocated to a signal component, which occurs more frequently, and a longer code may be allocated to a signal component, which occurs less frequently. In this manner, it is possible to suppress the redundancy of the image signal components and to compress the total amount of the image signal components. An example of encoding into the Huffman codes is shown in Table 4.

TABLE 4

| Data to be encoded | Probability of occurrence | Huffman code |
|---|---|---|
| 12 | 0.17915 | * 110010100 |
| 11 | 0.24725 | * 110010110 |
| 10 | 0.34762 | * 11000100 |
| 9 | 0.53324 | * 00001100 |
| 8 | 0.80575 | * 1100011 |
| 7 | 1.26047 | * 0000111 |
| 6 | 1.81047 | * 000001 |
| 5 | 2.59991 | * 11010 |
| 4 | 3.46648 | * 00110 |
| 3 | 5.00862 | * 1111 |
| 2 | 7.54548 | * 0010 |
| 1 | 11.69478 | * 101 |
| 0 | 27.29015 | * 01 |
| −1 | 11.69478 | * 100 |
| −2 | 7.54548 | * 0001 |
| −3 | 5.00862 | * 1110 |
| −4 | 3.46648 | * 00111 |
| −5 | 2.59991 | * 11011 |
| −6 | 1.81047 | * 000010 |
| −7 | 1.26047 | * 110000 |
| −8 | 0.80575 | * 1100100 |
| −9 | 0.53324 | * 00001101 |
| −10 | 0.34762 | * 11000101 |
| −11 | 0.24725 | * 110010111 |
| −12 | 0.17915 | * 110010101 |
| EXT | 1.71141 | * 110011 |

In the example described above, in cases where the data to be encoded falls outside of the range of −12 to +12, it is expressed in the form of the extension code (EXT)+the raw data. For example, in cases where the data to be encoded is 13, it is expressed as:

13 ⟶ 11001 00001101
         EXT    13

For example, in cases where the prediction errors serving as the data to be encoded range from the −255 level to the +255 level, it is desirable for improving the compressibility that the Huffman codes are allocated to all of the levels of the prediction errors. However, the prediction errors, which occur less frequently, e.g. the prediction errors falling outside the range of −12 to +12, should preferably be expressed in the form of EXT+the prediction error. In such cases, since these prediction errors occur less frequently, the compressibility is not adversely affected, and the encoding table becomes compact.

The compressed signal, which has been encoded in the manner described above is stored on the storage medium, such as an optical disk, in the image filing device 34. FIG. 21 shows an example of the signal stored on the storage medium. In FIG. 21, a11', Δa12', . . . respectively represent the compressed signal components obtained by encoding of a11, Δa12, . . . into the Huffman codes. TOI denotes the identification code, which indicates the beginning of the image, and TOL designates the identification code, which indicates the beginning of each scanning line (i.e. the block line).

The compressed signal stored on the storage medium is read therefrom when necessary, and used for reproduction of a visible image. How the visible image is reproduced will be briefly described hereinbelow. First, the compressed signal is read from the storage medium, and the decoding processing is conducted on the compressed signal. Specifically, the compressed signal is decoded to the prediction errors, or the like (i.e., a11, Δa12, Δa13, . . . , a21, Δa22, Δa23, . . . , a31, A32, Δa33, . . . ), which have not been subjected to the compression encoding, on the basis of the Huffman encoding table which was used when the compressed signal were created. Also, the representative image signal components of the respective blocks are calculated and restored from the prediction errors, or the like. The calculations are carried out with the formulas $a_{11}$, $a_{12}=a_{11}+\Delta a_{12}$, $a_{13}=a_{12}+\Delta a_{13}$, . . .
$a_{21}$, $a_{22}=a_{21}+\Delta a_{22}$, $a_{23}=a_{22}+\Delta a_{23}$, . . .
$a_{31}$, $a_{32}=a_{31}+\Delta a_{32}$, $a_{33}=a_{32}+\Delta a_{33}$, . . .

Thereafter, the component number restoring post-processing is conducted on the representative image signal components of the blocks, which have been decoded and restored in the manner described above. The number of the image signal components is thereby returned to the number of the image signal components of the original image signal Sd2'.

Figure 18B:
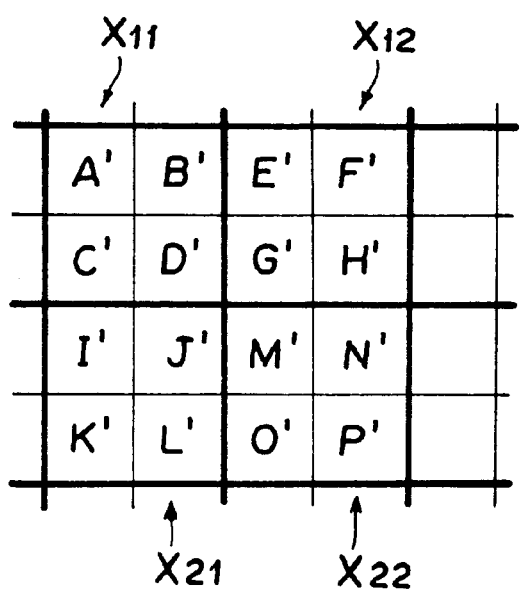
FIG. 18B is an explanatory view showing an example of component number restoring post-processing, which corresponds to the pre-processing shown in FIG. 18A.

FIG. 18B shows a decompressed image signal Se2, which has been obtained from the component number restoring post-processing. In FIG. 18B, restored image signal components A', E', I' and M', which represent the left top picture elements in the respective blocks X11, X12, X21 and X22, have already been restored as the representative image signal components in the manner described above. The restored image signal components are expressed as A'=a11, E'=a12, I'=a21, and M'=a22. For the purposes of restoring the image signal components representing the other picture elements, it is possible to employ any of various methods. For example, they may be restored by linear interpolation with respect to the horizontal and vertical directions.

With such a restoring method, the image signal components B', C', D', G' and J' shown in FIG. 18B can be decoded with the formulas $$B' = (A' + E')/2 = (a_{11} + a_{12})/2$$

$$C' = (A' + I')/2 = (a_{11} + a_{21})/2$$

$$G' = (E' + M')/2 = (a_{12} + a_{22})/2$$

$$J' = (I' + M')/2 = (a_{21} + a_{22})/2$$

$$D' = (C + G)/2 = (B + J)/2$$

$$= (A + E + I + M)/4$$

$$= (a_{11} + a_{12} + a_{21} + a_{22})/4$$

A visible image may then be reproduced on a CRT display device, or the like, on the basis of the restored signal components which have thus been obtained (of course, in this case, the restored signal components B', C', D', . . . obtained by the linear interpolation do not exactly coincide with the original image signal components B, C, D, . . . ).

Figure 22A:
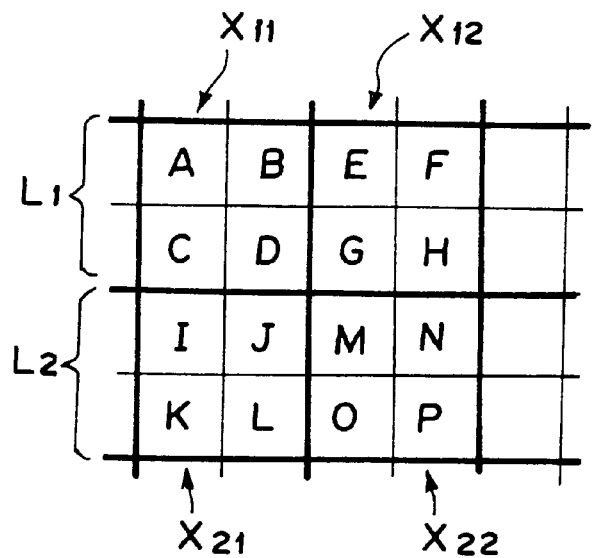
FIG. 22A is an explanatory view showing a different example of the component number decreasing pre-processing.

The aforesaid component number decreasing pre-processing may also be carried out with the method as shown in FIG. 22A. Specifically, as in the case of FIG. 18A, the radiation image is divided into blocks, each of which is composed of 2×2 picture elements. The mean value of the values of the image signal components representing the respective picture elements located in the block X11 is calculated as the representative image signal component a11 of the block X11. Also, in the same manner as that described above, mean values of the values of the image signal components representing the respective picture elements in the blocks X12, . . . , X21, X22, . . . are calculated as the representative image signal components a12, . . . , a21, a22, . . . of the respective blocks. These operations are carried out with the formulas $a_{11}$=(A+B+C+D)/4, $a_{12}$=(E+F+G+H)/4, . . .

$a_{21}$=(I+J+K+L)/4, $a_{22}$=(M+N+O+P)/4, . . . . Only the representative image signal components, which have thus been calculated, may be sampled. By way of example, in cases where the pre-processing has been carried out in accordance with this method, during the component number restoring post-processing in the aforesaid decompression processing, the restored representative image signal components a11, a12, . . . , a21, a22, . . . of the respective blocks may be employed as the image signal components corresponding to specific positions in the respective blocks, for example, the left top picture elements in the respective blocks. Also, the image signal components representing the other picture elements may be restored by carrying out the horizontal and vertical linear interpolation on the basis of the representative image signal components in the same manner as that described above.

Figure 22B:
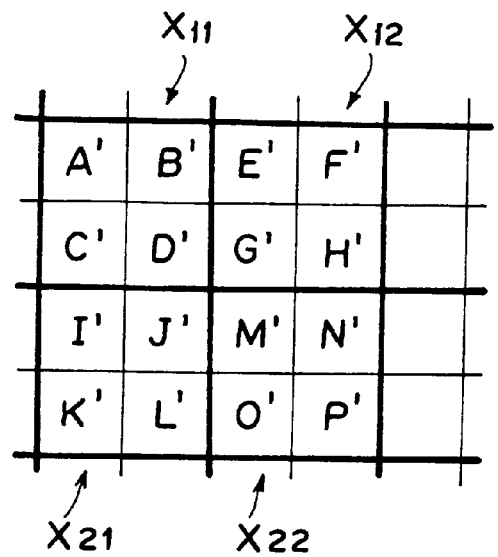
FIG. 22B is an explanatory view showing an example of the component number restoring post-processing, which corresponds to the component number decreasing pre-processing shown in FIG. 22A.

With this method, image signal components A', E', I' and M', which have been restored as shown in FIG. 22B by the component number restoring post-processing are expressed as A'=a11, E'=a12, I'=a21, and M'=a22. Also, image signal components B', C', D', G' and J' can be restored in the same manner as that shown in FIG. 18B.

In the component number decreasing pre-processing shown in FIGS. 18A and 22A, blocks are set with the same phases for each of the block lines L1, L2, and the representative image signal components of the respective blocks are sampled. Alternatively, the block setting should preferably be effected by shifting the phases for each of the block lines. This is because, when sampling is effected by shifting the phases, coarseness does not become visually perceptible and apparent sharpness can be improved as compared with the cases where sampling is effected without shifting the phases. Also, for example, in cases where a stationary grid for elimination of scattered radiation was used during the operation for recording the radiation image, if the image signal components are sampled with the same phases and the number thereof is thereby decreased, a moire pattern will readily occur on the restored image. On the other hand, when the image signal components are sampled by shifting the phases, it is possible to suppress the occurrence of the moire pattern.

Examples of sampling by shifting the phases, i.e. typical examples of the phase shift sampling, will hereinbelow be described with reference to FIGS. 23, 24A, 24B, 24C, 25A, 25B, and 25C.

Figure 23:
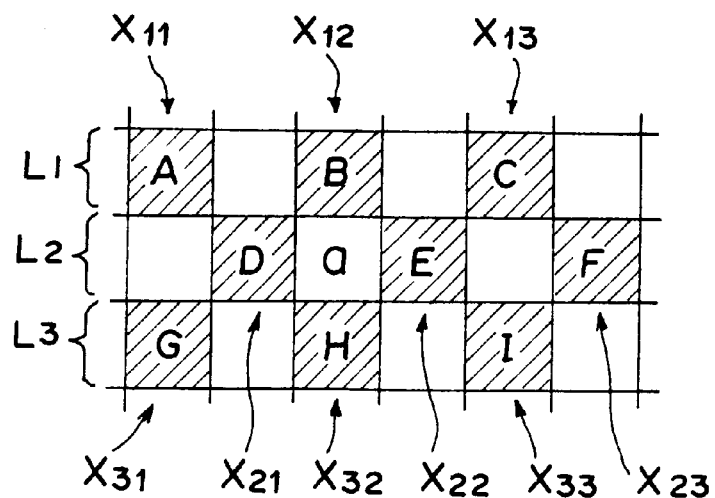
FIG. 23 is an explanatory view showing an example of a phase shift sampling type of component number decreasing pre-processing.

With the phase shift sampling shown in FIG. 23, a plurality of the block lines L1, L2, L3, . . . are set parallel to each other on the radiation image. On the block line L1, blocks X11, X12, X13, . . . , each of which is composed of a single picture element indicated by a single cell, are set such that they may be spaced a predetermined distance from each other (in this example, they are spaced the distance equal to the length of a single block from each other). On the block line L2, blocks X21, X22, X23, . . . , each of which is composed of a single picture element indicated by a single cell, are set such that they may be spaced the predetermined distance from each other. Also, on the block line L3, blocks X31, X32, X33, . . . , each of which is composed of a single picture element indicated by a single cell, are set such that they may be spaced the predetermined distance from each other. During the block setting, the phases of the blocks located along a block line are shifted from the phases of the blocks located along a neighboring block line. Only the representative image signal components a11, a12, a13, . . . , a21, a22, a23, . . . , a31, a32, a33, . . . , which have been calculated based on the image signal components representing the picture elements located in the thus set respective blocks, are sampled. In this case, as the representative image signal components a11, a12, a13, . . . , a21, a22, a23, . . . , a31, a32, a33, . . . , for example, the image signal components representing the picture elements located in the corresponding blocks may be directly employed as shown below.

$a_{11}$=A, $a_{12}$=B, $a_{13}$=C, . . .

$a_{21}$=D, $a_{22}$=E, $a_{23}$=F, . . .

$a_{31}$=G, $a_{32}$=H, $a_{33}$=I, . . .

In this example, when the component number restoring post-processing is carried out in the decompression processing, restoration of an image signal component corresponding to a picture element, for which no signal component is recorded, may be conducted by calculating the mean value of the values of the image signal components representing four surrounding picture elements. For example, the value of an image signal component "a" representing the picture element, which is surrounded by four blocks X12, X21, X22 and X32 in FIG. 23, may be calculated with the formula $a$=(B+D+E+H)/4

Figure 24A:
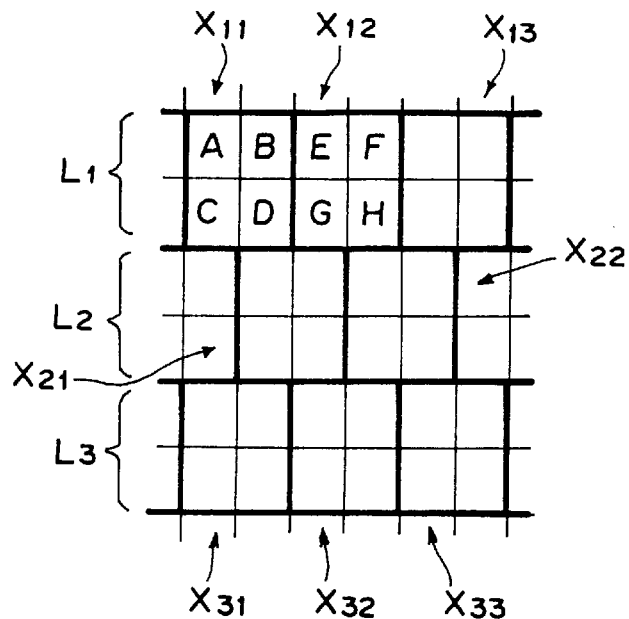
FIG. 24A is an explanatory view showing a different example of the phase shift sampling type of component number decreasing pre-processing.
Figure 24B:
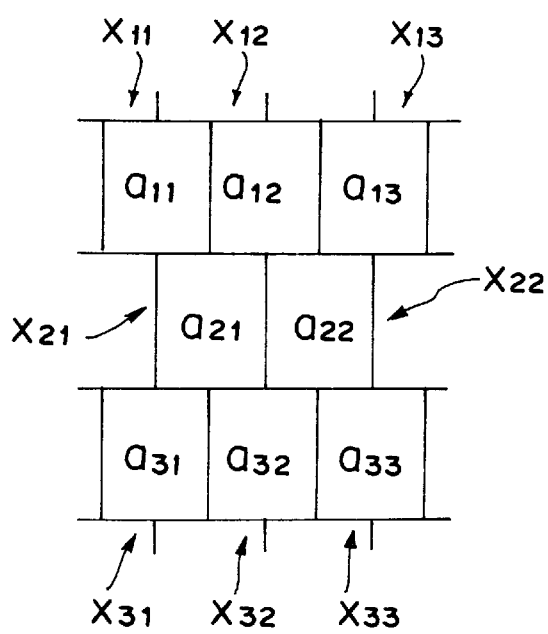
FIG. 24B is an explanatory view showing the representative image signal components of respective blocks which are set as shown in FIG. 24A.

In a different example of the phase shift sampling, the blocks, each of which is composed of 2×2 picture elements, are set as shown in FIG. 24A. Specifically, blocks X11, X12, X13, . . . , X21, X22, . . . , X31, X32, X33, . . . are set continuously along the block lines L1, L2 and L3 such that the phases of the blocks located along a block line may be shifted by one half of the length of a single block from the phases of the blocks located along a neighboring block line. Thereafter, as shown in FIG. 24B, the mean value of the values of the image signal components representing the four picture elements located in the block X11 is calculated and sampled as the representative image signal component a11 of the block X11. Also, in the same manner as that described above, mean values of the values of the image signal components representing the four picture elements in the blocks X12, X13, . . . are calculated and sampled as the representative image signal components a12, a13, . . . of the respective blocks. Further, in the same manner as that described above, mean values of the values of the image signal components representing the four picture elements in the respective blocks X21, X22, . . . , X31, X32, X33, . . . are calculated and sampled as the representative image signal components a21, a22, . . . , a31, a32, a33, . . . of the respective blocks. Specifically, for example, the values of the representative image signal components a11 and a12 are calculated with the formulas $a_{11}$=(A+B+C+D)/4, $a_{12}$=(E+F+G+H)/4

Figure 24C:
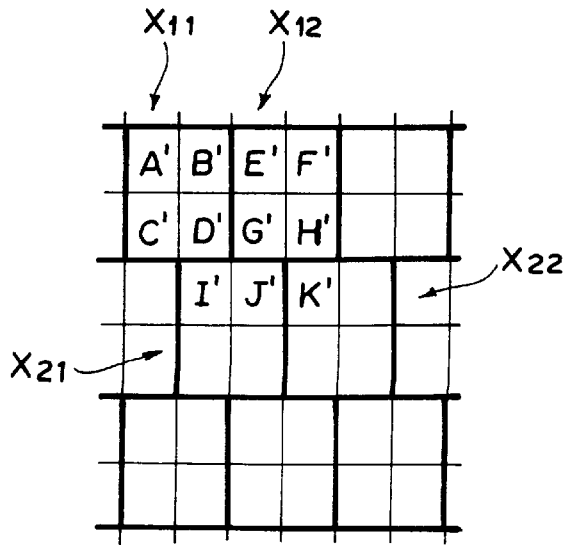
FIG. 24C is an explanatory view showing an example of the component number restoring post-processing, which corresponds to the component number decreasing pre-processing shown in FIG. 24A.

In such cases, as shown in FIG. 24C, when the component number restoring post-processing is to be carried out in the decompression processing, for example, the representative image signal components a11, a12, . . . , a21, a22, . . . , a31, a32, . . . of the respective blocks may be taken as the image signal components corresponding to specific positions in the respective blocks, e.g. as the image signal components representing the left top picture elements in the respective blocks. The image signal components representing the other picture elements may then be calculated and restored with the horizontal and vertical linear interpolation from the representative image signal components. These calculations are carried out with the formulas A'=$a_{11}$,
E'=$a_{12}$,
I'=$a_{21}$,
K'=$a_{22}$,
B'=(A'+E')/2=($a_{11}$+$a_{12}$)/2
D'=(B'+I')/2={($a_{11}$+$a_{12}$)/2+$a_{21}$}/2
J'=(I'+K')/2=($a_{21}$+$a_{22}$)/2
G'=(E'+J')/2={$a_{12}$+($a_{21}$+$a_{22}$)/2}/2

Figure 25A:
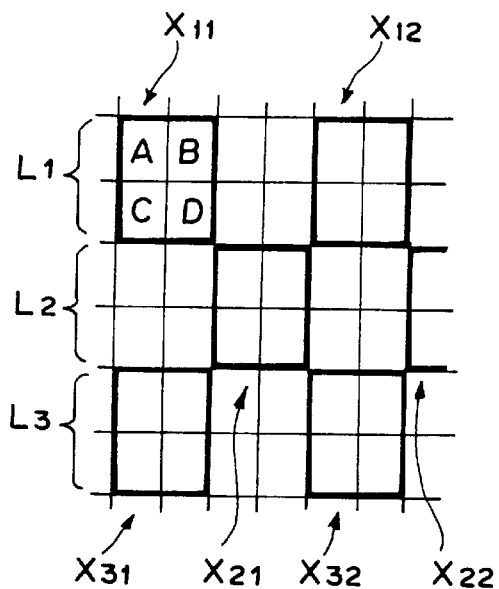
FIG. 25A is an explanatory view showing a further different example of the phase shift sampling type of component number decreasing pre-processing.
Figure 25B:
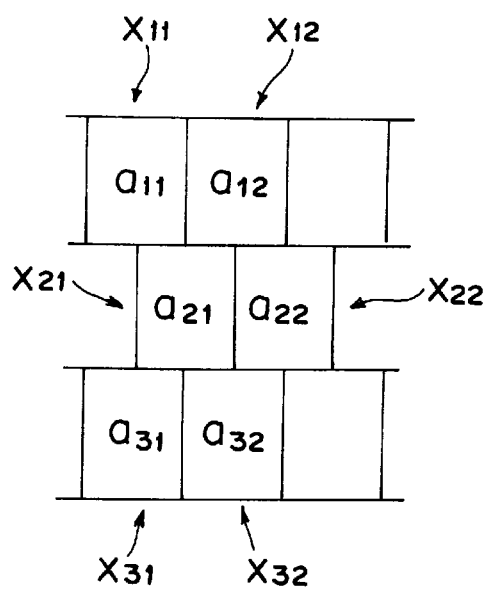
FIG. 25B is an explanatory view showing the representative image signal components of respective blocks which are set as shown in FIG. 25A.

In a further example of the phase shift sampling, the blocks, each of which is composed of 2×2 picture elements, are set as shown in FIG. 25A. Specifically, blocks X11, X12, . . . , X21, X22, . . . , X31, X32, . . . are set along the block lines L1, L2 and L3 such that the blocks located along each block line may be spaced a predetermined distance equal to the length of a single block from each other. The phases of the blocks located along a block line are shifted by the length of a single block from the phases of the blocks located along a neighboring block line. Thereafter, as shown in FIG. 25B, the mean value of the values of the image signal components representing the four picture elements located in the block X11 is calculated and sampled as the representative image signal component a11 of the block X11. Also, in the same manner as that described above, the mean value of the values of the image signal components representing the four picture elements in the block X12 is calculated and sampled as the representative image signal component a12 of the block X12. Further, in the same manner as that described above, mean values of the values of the image signal components representing the four picture elements in the respective blocks X21, X22, . . . , X31, X32, . . . are calculated and sampled as the representative image signal components a21, a22, . . . , a31, a32, . . . of the respective blocks. Specifically, for example, the value of the representative image signal component a11 is calculated with the formula $a_{11}$=(A+B+C+D)/4

Figure 25C:
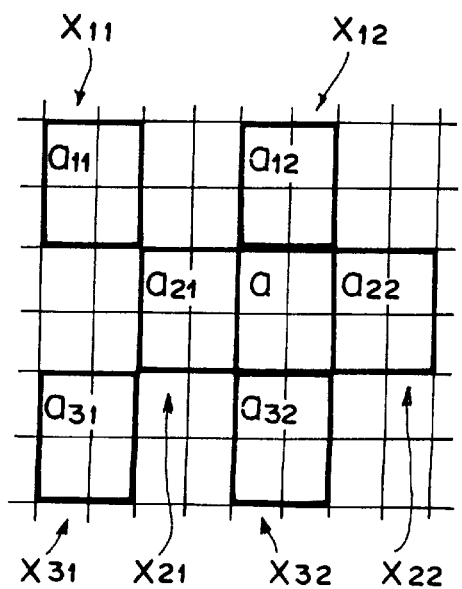
FIG. 25C is an explanatory view showing an example of the component number restoring post-processing, which corresponds to the component number decreasing preprocessing shown in FIG. 25A.

In such cases, as shown in FIG. 25C, when the component number restoring post-processing is to be carried out in the decompression processing, for example, the representative image signal components a11, a12, . . . , a21, a22, . . . , a31, a32, . . . of the respective blocks may be taken as the image signal components corresponding to specific positions in the respective blocks, e.g. as the image signal components representing the left top picture elements in the respective blocks. Thereafter, the mean value of the representative image signal components of the four blocks, which surround a 2×2 picture element region, is allocated as the image signal component representing the left top picture element of the 2×2 picture element region. For example, as the value of an image signal component "a" representing the left top picture element of the 22 picture element region, which is surrounded by the blocks X12, X21, X22, and X32, the value calculated with the formula a=($a_{12}$+$a_{21}$+$a_{22}$+$a_{32}$)/4 is allocated. Thereafter, image signal components representing the other picture elements may be calculated with horizontal and vertical linear interpolation from the representative image signal components a11, a12, . . . and the image signal component "a", which has been calculated on the basis of the representative image signal components.

The component number decreasing pre-processing may also be carried out in one of various other manners. For example, instead of the blocks, each of which is composed of 2×2 picture elements, being set as in the examples shown in FIGS. 18A, 22A, 24A and 25A, blocks, each of which is composed of n×n picture elements, wherein n represents an integer of 3 or larger, may be set. Also, in the examples shown in FIGS. 24B and 25B, the mean values of the values of the image signal components representing the picture elements in the respective blocks are taken as the representative image signal components of the blocks. Alternatively, as in the example of FIG. 18A, the image signal component representing the picture element, which is located at the specific position in the block, may be taken as the representative image signal component of the block. Further, in the examples of FIGS. 23 and 25A, the blocks are set in a checkered pattern, and the image signal components representing the other image portions are discarded. Alternatively, in cases where the blocks are set at some portions on the image and the image signal components representing the other image portions are discarded, the blocks may be set in one of various manners other than the checkered pattern.

Also, the aforesaid redundancy suppression encoding processing is not limited to the prediction encoding, and it is possible to employ any other processing, for example, encoding by orthogonal transformation, for this purpose. Further, in the prediction encoding, the prediction method is not limited to the previous value prediction, and it is possible to employ various other prediction methods, for example, two-dimensional prediction using the image signal components representing the neighboring picture elements. Encoding of the prediction errors is not limited to encoding into the Huffman codes, and any of other encoding methods may be employed for this purpose.

In the compressing process described above, before the redundancy suppression encoding processing is carried out on the image signal, the number of the image signal components of the image signal is decreased, i.e. the spatial resolution is decreased. Only the image signal, whose image signal components have been decreased, is then subjected to the redundancy suppression encoding processing. Therefore, the signal compressibility can be kept higher than when the redundancy suppression encoding processing is carried out without the pre-processing for decreasing the number of the image signal components of the image signal being conducted.

Studies carried out by the inventor revealed that, unlike other ordinary images, radiation images of human bodies, or the like, have characteristics such that important image information, such as the image information to be used in making diagnoses, falls within a low spatial frequency range and includes few high spatial frequency components. Therefore, even if the spatial resolution is made lower as described above and the high spatial frequency components are eliminated, the image quality, particularly, the effectiveness of the image in the efficient and accurate diagnosis of an illness, will not substantially become worse than when the density resolution is made lower.

Also, with this compressing process, the operation for compressing the image signal can be carried out more quickly than the compressing process described above, which is capable of restricting the occurrence of the moire.

Further, the digital image signal Sd2' has been subjected to the filtering processing and the resampling processing described above and, therefore, does not contain the image signal components representing the grid image 6. Therefore, even if the compressing process described above is carried out on the image signal Sd2', no moire will occur on the visible radiation image reproduced from the image signal Se2, which is obtained from the decompression processing carried out after the compressing process.

The signal generating system which carries out the filtering processing and the resampling processing for eliminating the grid image (i.e., in the aforesaid embodiment, the system which includes the second radiation image read-out apparatus 32) may be provided with a switch for selecting a mode, in which the filtering processing and the resampling processing are carried out, or a mode, in which the filtering processing and the resampling processing are not carried out. In such cases, the state of the switch for selecting one of these modes corresponds to the conditions, under which the image signal before being subjected to compression processing is generated. Therefore, the compressing process, which is to be employed, may be changed by being interlocked with the switch.

Embodiments of the method for reproducing a radiation image in accordance with the present invention will be described hereinbelow.

Figure 26:
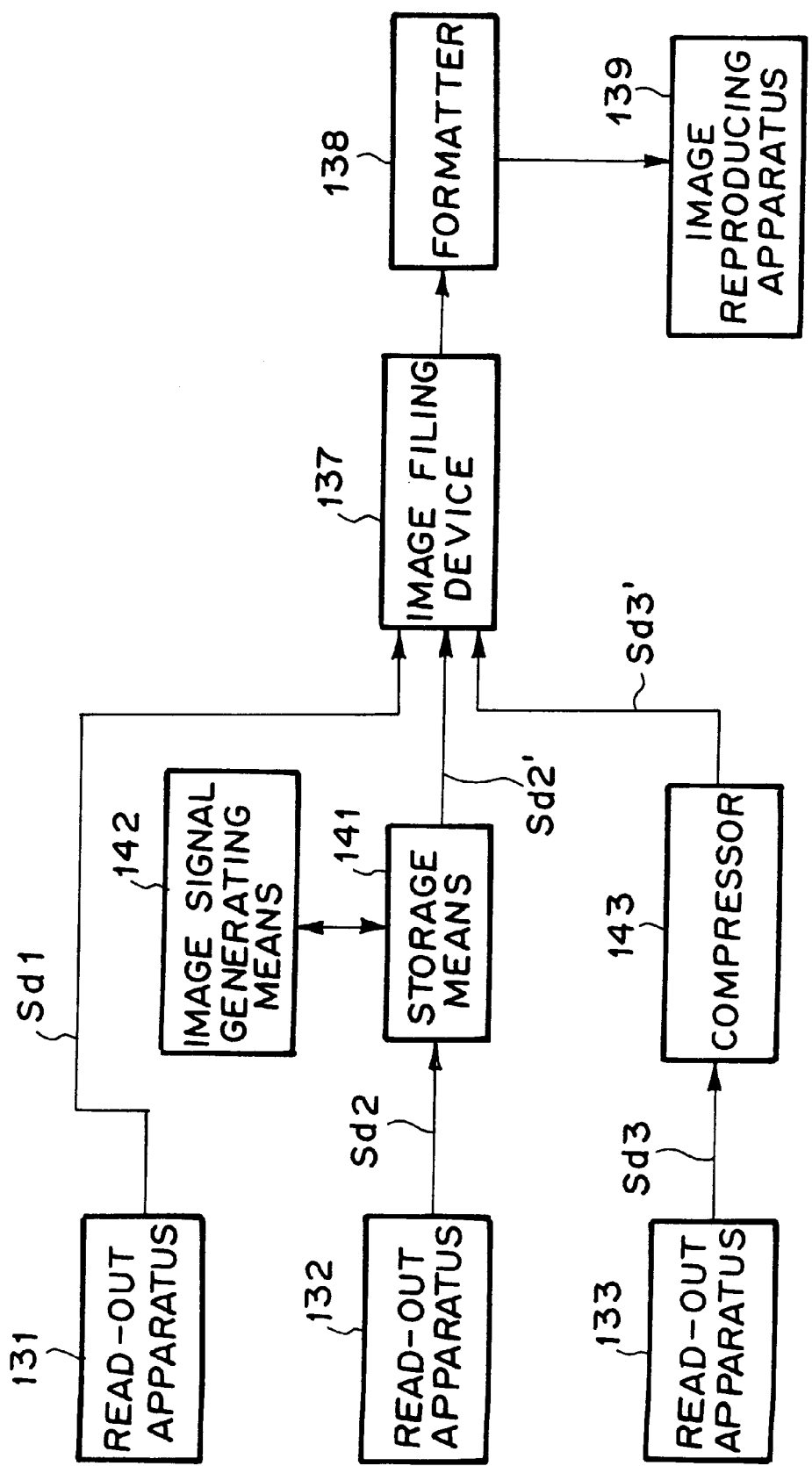
FIG. 26 is a block diagram showing a radiation image read-out and reproducing system for carrying out an embodiment of the method for reproducing a radiation image in accordance with the present invention.

FIG. 26 shows a radiation image read-out and reproducing system for carrying out an embodiment of the method for reproducing a radiation image in accordance with the present invention. In the radiation image read-out and reproducing system, a stimulable phosphor sheet is employed as a recording medium. First, a radiation image is stored on a stimulable phosphor sheet 11 in the same manner as that described above with reference to FIG. 2. As illustrated in FIG. 3, the radiation image comprises an object image 5 (indicated by the oblique lines) and a striped grid image 6 (indicated by vertical stripes) which corresponds to the grid 4 and which is superposed upon the object image 5.

A radiation image recording operation is often carried out without the grid 4 being used. In such cases, the striped grid image 6 is not recorded on the stimulable phosphor sheet 11.

The stimulable phosphor sheet 11, on which the radiation image has been stored in the manner described above, is then subjected to an operation for reading out the radiation image in a first radiation image read-out apparatus 131, a second radiation image read-out apparatus 132, or a third radiation image read-out apparatus 133 of the radiation image read-out and reproducing system shown in FIG. 26. Both the stimulable phosphor sheet 11, on which the radiation image has been stored by using the grid 4, and the stimulable phosphor sheet 11, on which the radiation image has been stored without the grid 4 being used, are supplied into the radiation image read-out apparatuses 131, 132, and 133. The first radiation image read-out apparatus 131 has the structure shown in FIG. 4. The radiation image is read out from the stimulable phosphor sheet 11 in the same manner as that described above with reference to FIG. 4.

As described above, the analog output signal S generated by the photomultiplier 23 includes signal components falling within the spatial frequency region above the spatial frequency fss=2.5 (cycles/mm), which is the maximum of a desired spatial frequency range necessary for the reproduction of a visible radiation image having good image quality. Particularly, in cases where the analog output signal S has been detected from the stimulable phosphor sheet 11 on which the radiation image was stored by using the grid 4, the analog output signal S includes the signal components, which represents the grid image 6 shown in FIG. 3 and which fall within the spatial frequency region above the spatial frequency fss. The signal components representing the grid image 6 adversely affect the image quality of a reproduced visible image of the object 3 and should be reduced or eliminated. In this embodiment, the spatial frequency of the grid image is assumed to be 4 cycles/mm.

The analog output signal S is logarithmically amplified by the logarithmic amplifier 26. In the A/D converter 28, the amplified analog output signal S is sampled at predetermined sampling intervals, and the sampled image signal is digitized into the digital image signal Sd1. In the first radiation image read-out apparatus 131, the analog output signal S is sampled by the A/D converter 28 at sampling intervals of $\Delta x=1/(2 \cdot fss)=0.2$ (mm), i.e. is sampled five times per mm. Also, no operation for eliminating the grid image 6 is carried out. Therefore, it often occurs that the image signal Sd1 contains the signal components, which represents the grid image 6. A code, which represents that the image signal has been obtained with the first radiation image read-out apparatus 131, is added to the image signal Sd1. Thereafter, the image signal Sd1 is stored on a storage medium of an image filing device 137, such as an optical disk unit.

The second radiation image read-out apparatus 132 and the third radiation image read-out apparatus 133 shown in FIG. 26 have the same basic structure as that of the first radiation image read-out apparatus 131. Digital image signals (original image signals) Sd2 and Sd3 are respectively obtained from the second radiation image read-out apparatus 132 and the third radiation image read-out apparatus 133.

In the second radiation image read-out apparatus 132, an analog output signal S is sampled by the A/D converter 28 at sampling intervals of $\Delta x=0.1$ (mm), i.e. is sampled ten times per mm. The digital image signal (the original image signal) Sd2 obtained from the A/D converter 28 is stored in a storage means 141. The image signal Sd2 is then read from the storage means 141 and is fed into an image signal generating means 142. In the image signal generating means 142, the image signal Sd2 is subjected to filtering processing for eliminating the signal components corresponding to the spatial frequency of 4 cycles/mm of the grid image 6. FIG. 5 shows the characteristics of the filtering processing. The image signal Sd2, which has been obtained from the filtering processing, is then resampled in the image signal generating means 142. During the resampling processing, the image signal Sd2 is sampled at sampling intervals of $\Delta x=0.2$ (mm), i.e. is sampled five times per mm.

The filtering processing and the resampling processing are described in detail in Japanese Unexamined Patent Publication No. 3(1991)-114039. In cases where the filtering processing and the resampling processing are carried out, even if the original image signal Sd2 is the one which has been detected from a stimulable phosphor sheet 11 having the radiation image stored thereon by using the grid 4, basically, a digital image signal Sd2' obtained from the filtering processing and the resampling processing will not contain the components representing the grid image 6. The image signal Sd2' is stored in the storage means 141. Thereafter, a code, which represents that the image signal has been subjected to the processing by the image signal generating means 142, is added to the image signal Sd2', and the image signal Sd2' is then stored on the storage medium in the image filing device 137.

The digital image signal Sd3, which has been obtained from the third radiation image read-out apparatus 133, is fed into a compressor 143. The compressor 143 carries out irreversible compression processing on the digital image signal Sd3 in order to decrease the amount thereof. By way of example, as the irreversible compression processing, a combination of prediction encoding and Huffman encoding, or the like, may be carried out. A digital image signal Sd3' is obtained from the compressor 143. The amount of the digital image signal Sd3' is smaller than the amount of the image signal Sd3. A code, which represents that the image signal has been subjected to the processing in the compressor 143, is added to the image signal Sd3'. The image signal Sd3' is then stored on the storage medium in the image filing device 137.

The digital image signals Sd1, Sd2', and Sd3' are then read from the storage medium of the image filing device 137 and fed into a formatter 138. The formatter 138 carries out predetermined interpolation processing on the digital image signals Sd1, Sd2', and Sd3'. Image signals obtained from the formatter 138 are fed into an image reproducing apparatus 139, which may be constituted of a CRT display device, a light beam scanning recording apparatus, or the like. The image reproducing apparatus 139 reproduces a visible radiation image from the digital image signal Sd1, Sd2', or Sd3'.

In the formatter 138, the interpolation processing (or the thinning-out processing) is carried out with a predetermined scale of enlargement or reduction on the digital image signal Sd1, Sd2', or Sd3'. As a result, a visible radiation image, which has been enlarged or reduced to a predetermined scale, is reproduced by the image reproducing apparatus 139. As for the image signal Sd3' which has been subjected to the compression processing, the interpolation processing also serves as the decompression processing.

Figure 27A:
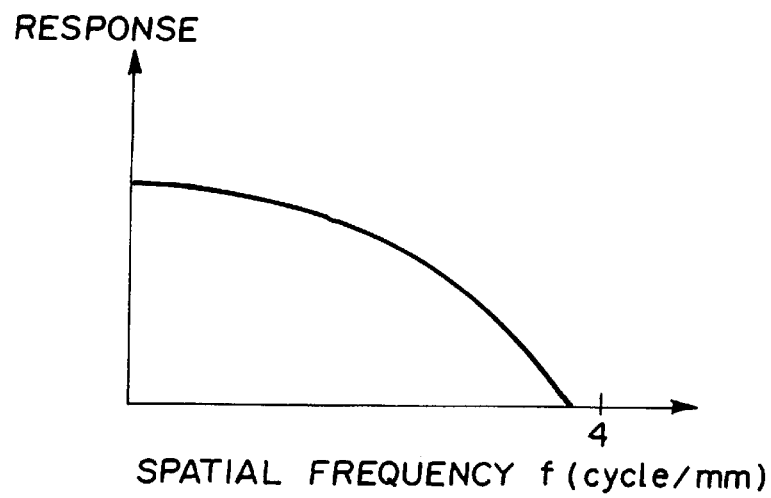
FIGS. 27A, 27B, and 27C are graphs showing frequency response characteristics of image signals obtained from interpolation processing.

Also, as for the digital image signal Sd1 having the code, which represents that the image signal has been obtained with the first radiation image read-out apparatus 131, the formatter 138 carries out interpolation processing of the first order. FIG. 27A shows the spatial frequency response characteristics of the interpolation processing of the first order. As illustrated in FIG. 27A, in cases where the interpolation processing is carried out such that the high frequency region, which is not lower than 4 cycles/mm, may be eliminated, even if the image signal Sd1 is the one which has been detected from the stimulable phosphor sheet 11 having the radiation image stored thereon by using the grid 4, the image signal components representing the grid image 6 can be eliminated from the image signal Sd1. Therefore, no moire occurs on a visible radiation image reproduced from the image signal Sd1, which has been obtained from the interpolation processing. In lieu of the interpolation processing of the first order, interpolation processing of a higher order may be carried out wherein the coefficients are set such that the high frequency region may be eliminated.

Figure 27B:
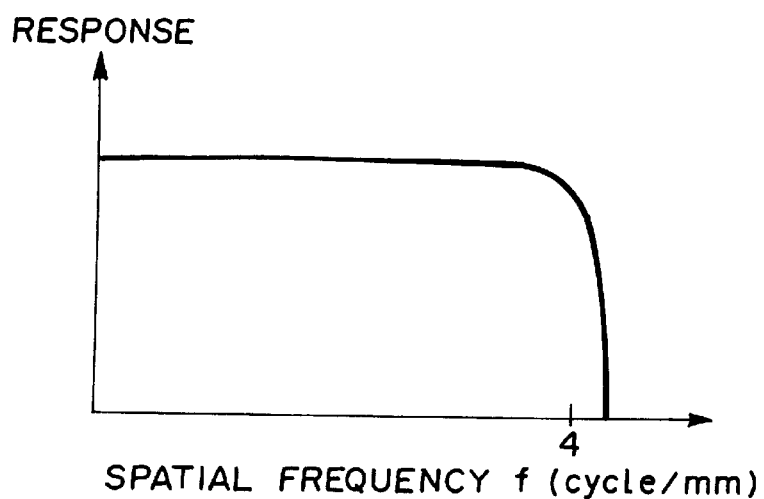

As for the digital image signal Sd2' having the code, which represents that the image signal has been subjected to the processing by the image signal generating means 142, the formatter 138 carries out interpolation processing of a higher order, e.g. of the third order. FIG. 27B shows the spatial frequency response characteristics of the interpolation processing of a higher order. In cases where the interpolation processing of a higher order is employed, the sharpness of the visible radiation image reproduced from the image signal Sd2', which has been obtained from the interpolation processing, can be prevented from becoming lower. Also, the digital image signal Sd2' before being subjected to the interpolation processing has been subjected to the filtering processing and the resampling processing and, therefore, does not contain the image signal components representing the grid image 6. Therefore, no moire occurs on the visible radiation image reproduced from the image signal Sd2', which has been obtained from the interpolation processing.

Figure 27C:
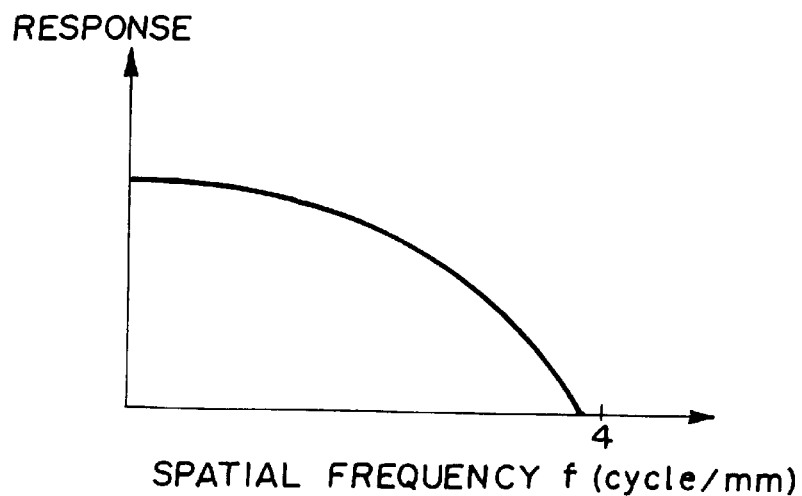

As for the digital image signal Sd3' having the code, which represents that the image signal has been subjected to the processing in the compressor 143, the formatter 138 carries out interpolation processing of the first order. FIG. 27C shows the spatial frequency response characteristics of the interpolation processing of the first order. As described above, an artifact, which occurs when irreversible compression processing is carried out on an image signal, is unevenly distributed in the high spatial frequency region. Therefore, as for the image signal Sd3' having been generated by being subjected to the irreversible compression processing, the interpolation processing of the first order may be employed. In this manner, an artifact can be prevented from occurring on the reproduced radiation image.

The signal generating system which carries out the filtering processing and the resampling processing for eliminating the grid image (i.e., in the aforesaid embodiment of the method for reproducing a radiation image in accordance with the present invention, the system which includes the second radiation image read-out apparatus 132) may be provided with a switch for selecting a mode, in which the filtering processing and the resampling processing are carried out, or a mode, in which the filtering processing and the resampling processing are not carried out. In such cases, the state of the switch for selecting one of these modes corresponds to the conditions, under which the image signal before being subjected to interpolation processing is generated. Therefore, the characteristics of the interpolation processing may be changed by being interlocked with the switch.

What is claimed is:

1. A method for compressing an image signal representing a radiation image, which comprises the steps of:

detecting the image signal by reading out the radiation image which has been recorded on a recording medium;

generating a conditioned image signal according to one condition of a set of conditions; and compressing the conditioned image signal into a compressed image signal using a compression process which is chosen depending upon said one condition.

2. A method for compressing an image signal as defined in claim 1 wherein the set of conditions includes: eliminating image signal components representing a grid image due to a grid, said grid being used during an operation for recording the radiation image.

3. A method for compressing an image signal as defined in claim 1 wherein the recording medium on which the radiation image has been stored is a stimulable phosphor sheet.

4. A method for compressing an image signal as defined in claim 3 wherein the image signal representing the radiation image is obtained by exposing the stimulable phosphor sheet to stimulating rays, which cause the stimulable phosphor sheet to emit light in proportion to an amount of energy stored thereon during exposure of the stimulable phosphor sheet to radiation, and photoelectrically detecting the emitted light.

5. A method for compressing an image signal as defined in claim 4 wherein the stimulating rays are a laser beam.

6. A method for compressing an image signal as defined in claim 1 wherein the radiation image has been recorded on photographic film.

7. An apparatus for compressing an image signal representing a radiation image, comprising:

means for detecting the image signal by reading out the radiation image which has been recorded on a recording medium;

means for generating a conditioned image signal according to one condition of a set of conditions;

means for compressing said conditioned image signal into a compressed image signal using one of a plurality of compressing processes; and means for choosing said one compressing process, which is to be employed during compression processing carried out on said conditioned image signal, in accordance with said one condition.

8. An apparatus for compressing an image signal as defined in claim 7 wherein the set of conditions includes: eliminating image signal components representing a grid image due to a grid, said grid being used during an operation for recording the radiation image.

9. An apparatus for compressing an image signal as defined in claim 7 wherein the recording medium on which the radiation image has been stored is a stimulable phosphor sheet.

10. An apparatus for compressing an image signal as defined in claim 9 wherein the image signal representing the radiation image is obtained by exposing the stimulable phosphor sheet to stimulating rays, which cause the stimulable phosphor sheet to emit light in proportion to an amount of energy stored thereon during exposure of the stimulable phosphor sheet to radiation, and photoelectrically detecting the emitted light.

11. An apparatus for compressing an image signal as defined in claim 10 wherein the stimulating rays are a laser beam.

12. An apparatus for compressing an image signal as defined in claim 7 wherein the radiation image has been recorded on photographic film.

13. A method for reproducing a radiation image, comprising the steps of:

detecting an image signal by reading out the radiation image from a recording medium on which the radiation image has been recorded, generating a conditioned image signal from said image signal according to one condition of a set of conditions, generating an interpolated image signal from said conditioned signal according to an interpolation process which is chosen depending upon said one condition, and reproducing a radiation image from the interpolated image signal.

14. A method for reproducing a radiation image as defined in claim 13 wherein the set of conditions includes: subjecting said image signal to filtering processing and resampling processing and subjecting the image signal to irreversible compression processing.

15. A method for reproducing a radiation image as defined in claim 13 wherein characteristics of the interpolation process include an order of coefficients in the interpolation process and values of the coefficients.

16. A method for reproducing a radiation image as defined in claim 13 wherein the recording medium on which the radiation image has been stored is a stimulable phosphor sheet.

17. A method for reproducing a radiation image as defined in claim 16 wherein the image signal representing the radiation image is obtained by exposing the stimulable phosphor sheet to stimulating rays, which cause the stimulable phosphor sheet to emit light in proportion to an amount of energy stored thereon during exposure of the stimulable phosphor sheet to radiation, and photoelectrically detecting the emitted light.

18. A method for reproducing a radiation image as defined in claim 17 wherein the stimulating rays are a laser beam.

19. A method for reproducing a radiation image as defined in claim 13 wherein the radiation image has been recorded on photographic film.

20. An apparatus for reproducing a radiation image, which is provided with means for generating an image signal by reading out the radiation image from a recording medium on which the radiation image has been recorded, means for generating a conditioned image signal from said image signal according to one condition of a set of conditions, means for generating an interpolated image signal from said conditioned image signal using interpolation processing, and means for reproducing a radiation image from said interpolated image signal, wherein the improvement comprises the provision of means for changing characteristics of the interpolation processing in accordance with said one condition.

21. An apparatus for reproducing a radiation image as defined in claim 20 wherein the set of conditions includes: subjecting the image signal to filtering processing and resampling processing and subjecting the image signal to irreversible compression processing.

22. An apparatus for reproducing a radiation image as defined in claim 20 wherein characteristics of the interpolation processing include an order of coefficients in the interpolation processing and values of the coefficients.

23. An apparatus for reproducing a radiation image as defined in claim 20 wherein the recording medium on which the radiation image has been stored is a stimulable phosphor sheet.

24. An apparatus for reproducing a radiation image as defined in claim 23 wherein the image signal representing the radiation image is obtained by exposing the stimulable phosphor sheet to stimulating rays, which cause the stimulable phosphor sheet to emit light in proportion to an amount of energy stored thereon during exposure of the stimulable phosphor sheet to radiation, and photoelectrically detecting the emitted light.

25. An apparatus for reproducing a radiation image as defined in claim 24 wherein the stimulating rays are a laser beam.

26. An apparatus for reproducing a radiation image as defined in claim 20 wherein the radiation image has been recorded on photographic film.

* * * * *